United States Patent
Saiki et al.

(10) Patent No.: US 8,596,150 B2
(45) Date of Patent: Dec. 3, 2013

(54) ANALYTICAL DEVICE WITH MIXING CAVITY

(75) Inventors: Hiroshi Saiki, Ehime (JP); Tomohiro Kijima, Ehime (JP); Kenji Ishibashi, Ehime (JP); Kouzou Tagashira, Ehime (JP)

(73) Assignee: Panasonic Corporation, Osaka (JP)

( * ) Notice: Subject to any disclaimer, the term of this patent is extended or adjusted under 35 U.S.C. 154(b) by 417 days.

(21) Appl. No.: 13/056,917

(22) PCT Filed: Jun. 30, 2009

(86) PCT No.: PCT/JP2009/003008
§ 371 (c)(1),
(2), (4) Date: Jan. 31, 2011

(87) PCT Pub. No.: WO2010/103579
PCT Pub. Date: Sep. 16, 2010

(65) Prior Publication Data
US 2011/0126646 A1     Jun. 2, 2011

(30) Foreign Application Priority Data
Mar. 12, 2009 (JP) ................ 2009-058820

(51) Int. Cl.
*G01N 1/00* (2006.01)
*G01N 9/30* (2006.01)
*B01L 3/00* (2006.01)
*G01N 35/00* (2006.01)

(52) U.S. Cl.
USPC ............. 73/864.83; 422/72; 422/503; 436/45

(58) Field of Classification Search
USPC ........ 73/864.81, 864.83; 422/72, 503; 436/45
See application file for complete search history.

(56) References Cited

U.S. PATENT DOCUMENTS

| 5,186,896 A * | 2/1993 | Bouchee et al. ................ 422/72 |
| 6,506,344 B1 * | 1/2003 | Fickenscher et al. ........... 422/72 |
| 7,727,472 B2 | 6/2010 | Nagaoka et al. |
| 2008/0056949 A1 * | 3/2008 | Lee et al. ........................ 422/72 |

FOREIGN PATENT DOCUMENTS

| CN | 1800858 | 7/2006 |
| JP | 10-501340 | 2/1998 |
| JP | 2006-145451 | 7/2006 |
| JP | 2007-021450 | 2/2007 |
| JP | 2009-031116 | 2/2009 |
| WO | 95/33986 | 12/1995 |
| WO | 2007/052648 | 5/2007 |

* cited by examiner

*Primary Examiner* — Hezron E Williams
*Assistant Examiner* — Nathaniel Kolb
(74) *Attorney, Agent, or Firm* — Hamre, Schumann, Mueller & Larson, P.C.

(57) ABSTRACT

An inlet (37a) of a capillary tube channel that feeds a liquid from a mixing cavity (39) to measurement spots is formed near one (4) of the wall surfaces of the upper and lower surfaces of the mixing cavity (39) situated in a direction of oscillation for mixing. On the other wall surface (3), a level difference (39a) is formed such that an inner gap is larger than an outer gap in the mixing cavity (39), so that a solution is reliably fed from the mixing cavity to the measurement cells.

12 Claims, 37 Drawing Sheets

FIG. 2
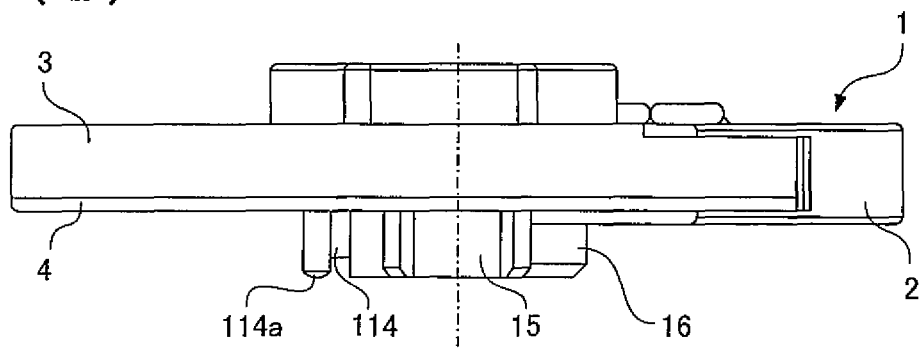
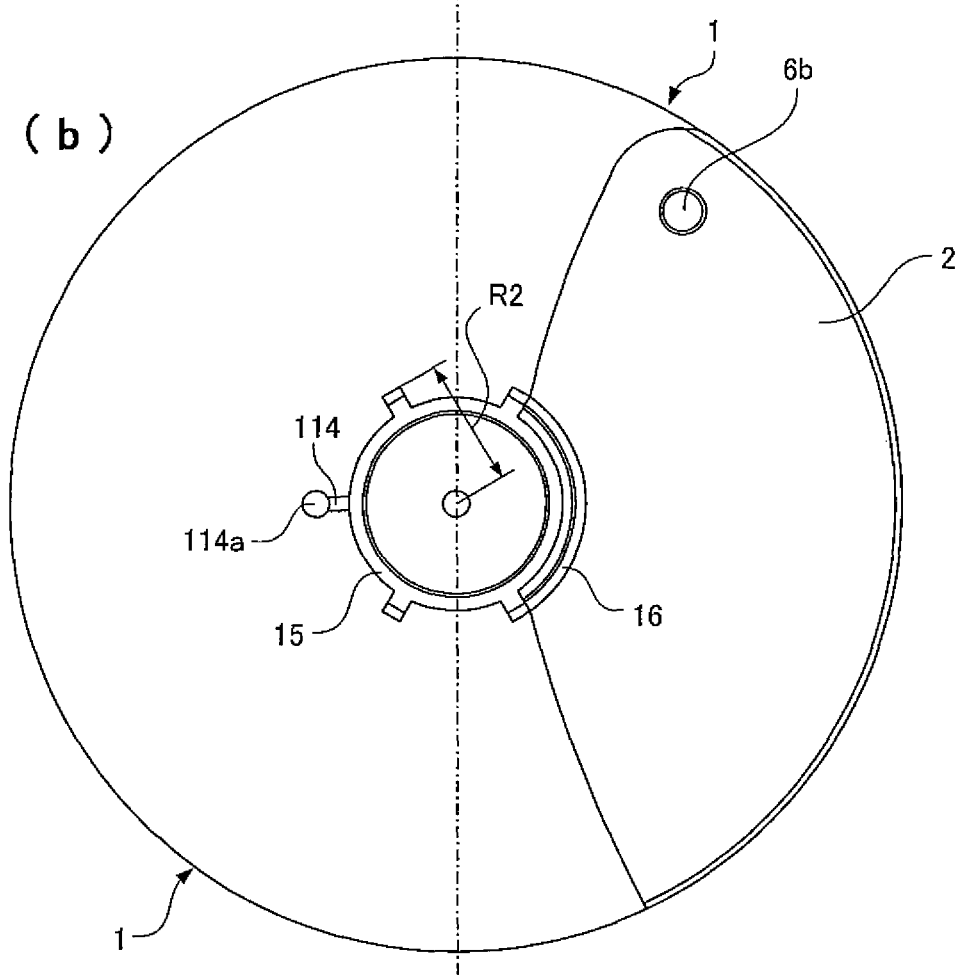

FIG. 19
(a)
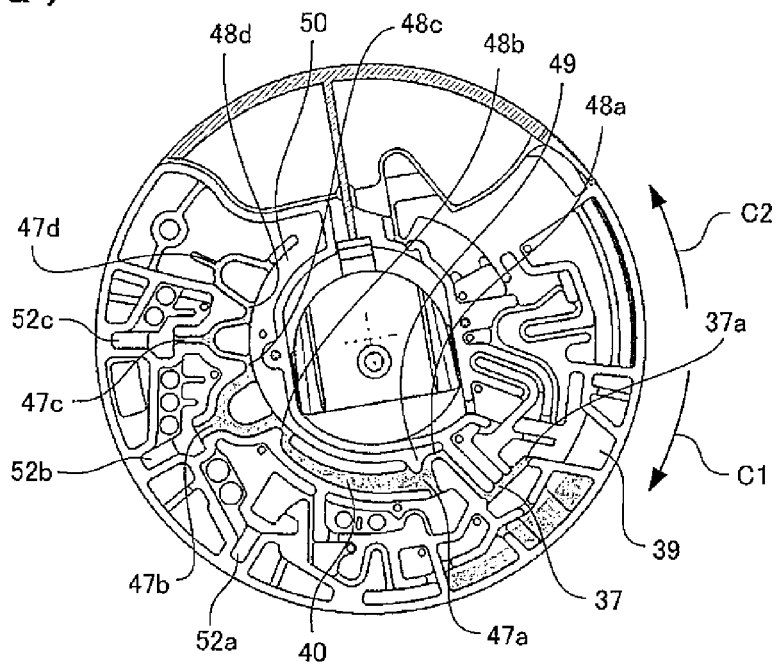
(b)
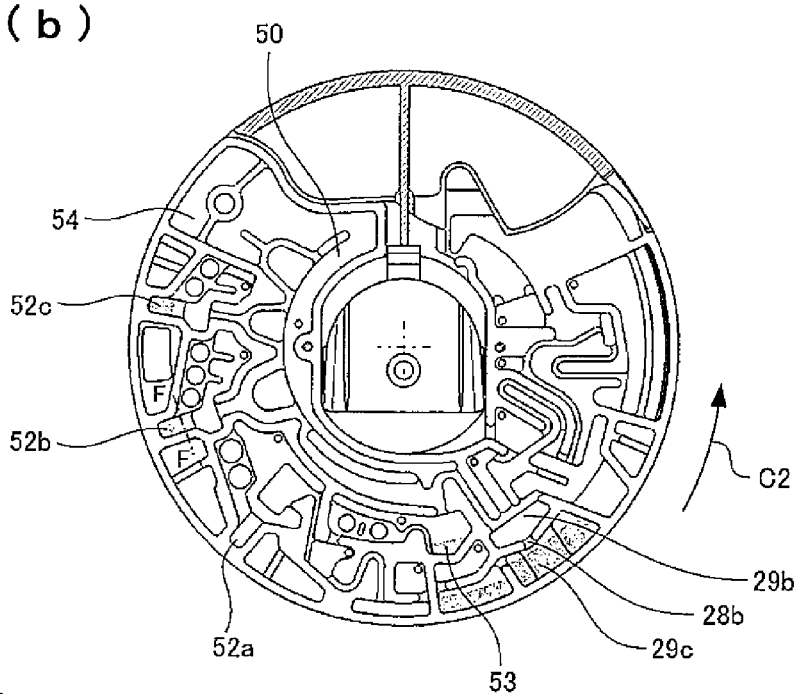

FIG. 20
(a)
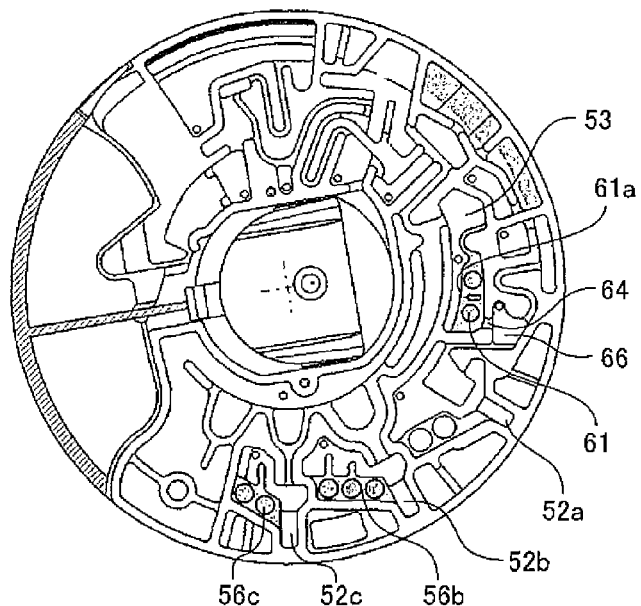
(b)
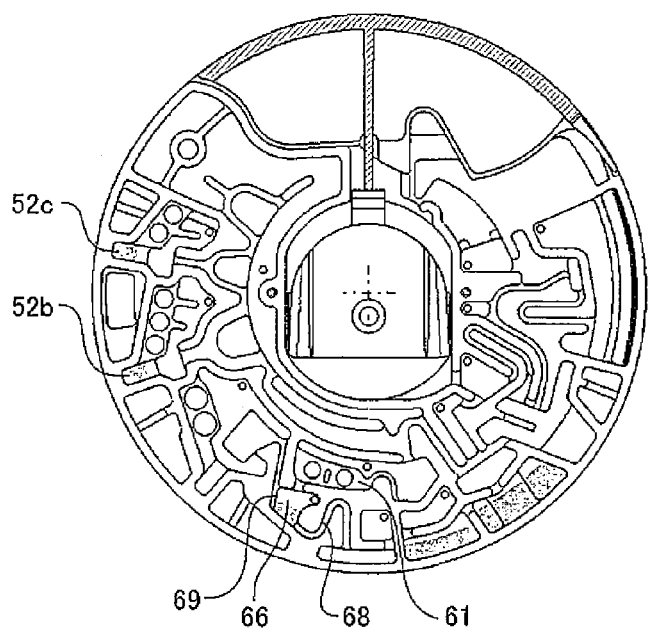

FIG. 21
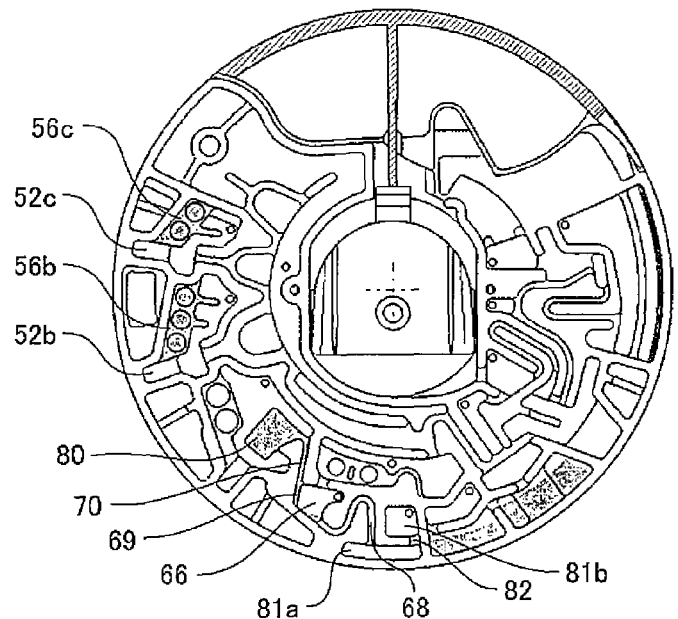
(a)
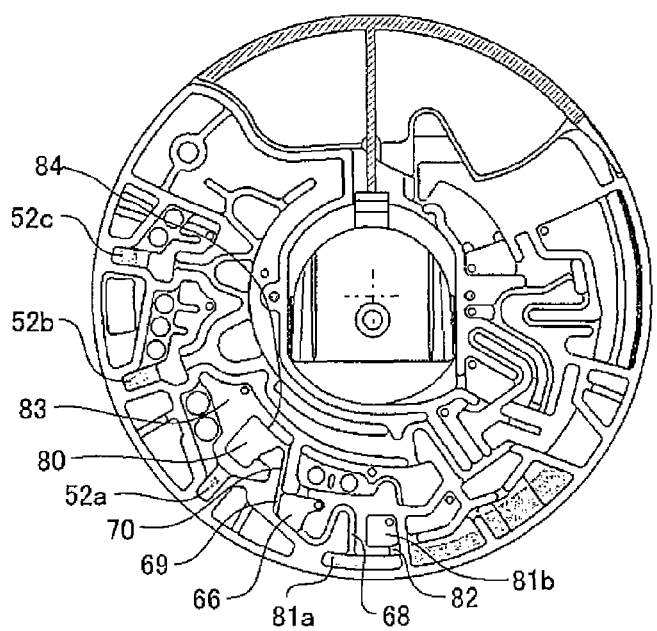
(b)

FIG. 22
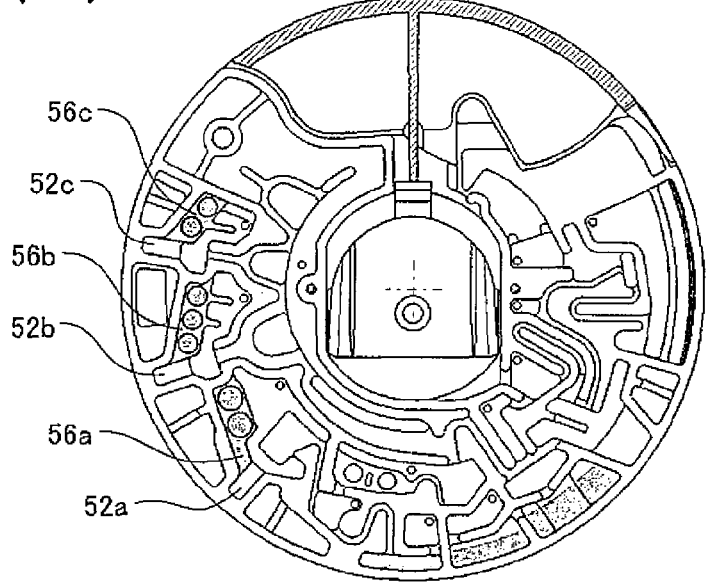
(a)
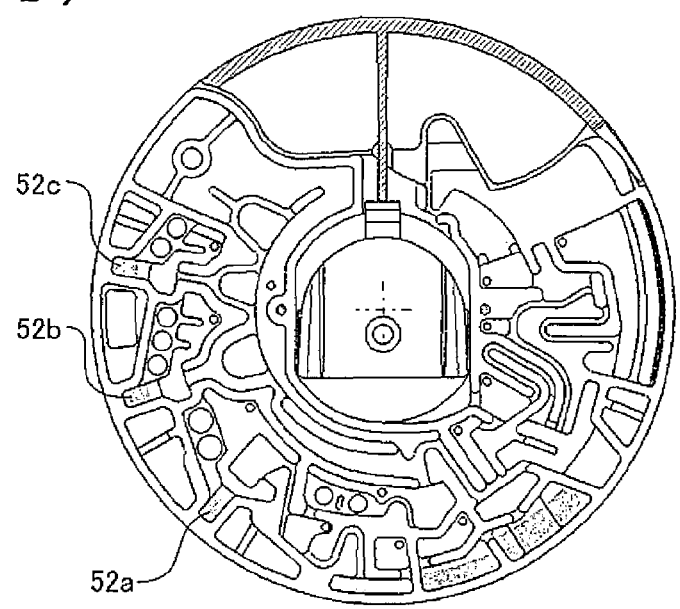
(b)

FIG. 26
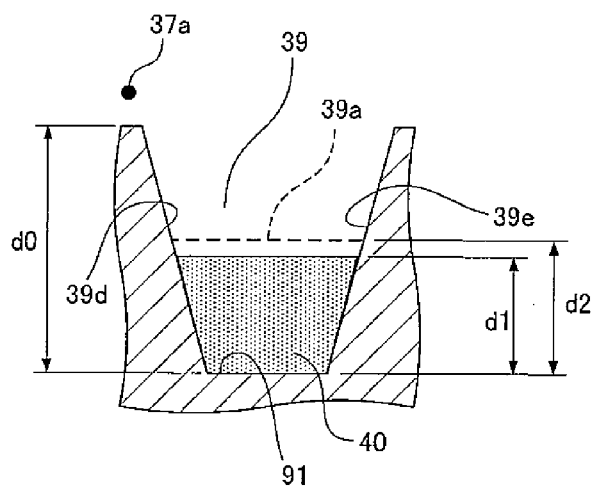
(a)
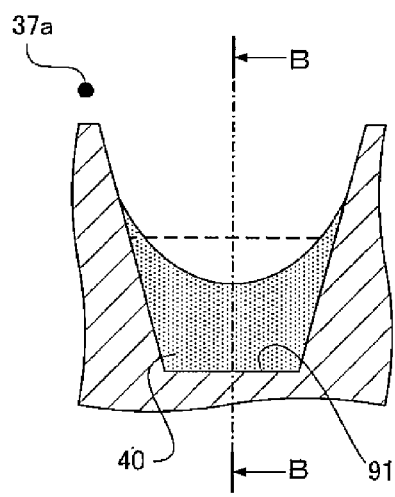
(b)
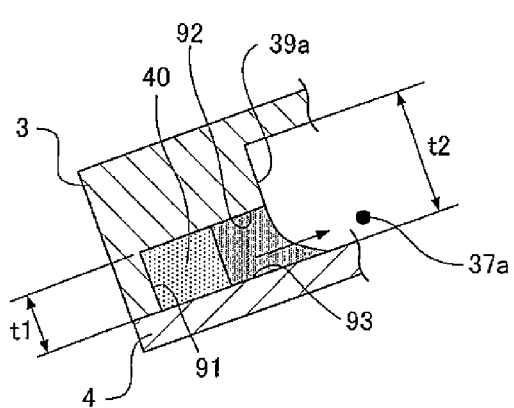
(c)

F-F SECTIONAL VIEW

ANALYTICAL DEVICE WITH MIXING CAVITY

TECHNICAL FIELD

The present invention relates to an analytical device used for analyzing a liquid collected from an organism or the like.

BACKGROUND ART

In the related art, a liquid collected from an organism or the like is analyzed by a known analyzing method using an analytical device having fluid channels formed therein. The analytical device can control a fluid with a rotator. By using a centrifugal force, the analytical device can dilute a sample liquid, measure a solution, separate a solid component, transfer and distribute a separated fluid, and mix the solution and reagents, thereby enabling various biochemical analyses.

Patent literature 1 describes an analytical device for transferring a solution by a centrifugal force. As shown in FIG. 38, a diluent in a diluent measuring chamber 214 and plasma in a separating chamber 215 are transferred to a mixing cavity 218 through siphon passages 216 and 217 by a centrifugal force, and are agitated by adjusting a rotation speed. After that, the diluent and the plasma are transferred to measurement cells 220 through a siphon passage 219.

CITATION LIST

Patent Literature

Patent Literature 1: National Publication of International Patent Application No. 10-501340

SUMMARY OF INVENTION

Technical Problem

In the configuration of the related art, however, it is necessary to agitate the diluent and plasma transferred in the mixing cavity 218 without stopping the rotation. In the presence of a centrifugal force, it is not possible to sufficiently agitate a solution in the inner and outer sides of the mixing cavity 218. Further, during the transfer from the mixing cavity 218 to the measurement cells 220, the solution partially remains in the siphon passage 219 and thus the quantity of the solution has to be larger than the required quantity of the measurement cells 220. Moreover, an oscillating operation involving no rotation may cause the mixed solution to flow backward to the siphon passage 217 or cause whole blood to flow from the separating chamber 215 afterward, adversely affecting the accuracy of measurement.

An object of the present invention is to provide an analytical device that can reliably feed a solution from a mixing cavity to measurement cells.

Another object of the present invention is to provide a reliable analytical device that can prevent backflow of liquid and inflow of liquid afterward when performing an oscillating operation while stopping the rotations of the analytical device.

Solution to Problem

An analytical device of the present invention is an analytical device having a microchannel structure in which a first liquid and a second liquid are mixed in a mixing cavity and transferred to measurement cells by a centrifugal force, the analytical device being used for reading that accesses the liquid in the measurement cells, wherein the mixing cavity has an inner surface including side walls arranged in the direction of oscillation for the mixing and upper and lower surfaces opposed to each other between the side walls, the analytical device includes a passage inlet for feeding the liquid from the mixing cavity to the measurement spots, the passage inlet being formed near one of the wall surfaces of the upper and lower surfaces, and the mixing cavity includes a level difference on the other wall surface of the upper and lower surfaces of the mixing cavity such that an inner gap is larger than an outer gap in the mixing cavity.

An analytical device of the present invention is an analytical device having a microchannel structure in which a first liquid and a second liquid are mixed in a mixing cavity and transferred to measurement cells by a centrifugal force, the analytical device being used for reading that accesses the liquid in the measurement cells, wherein the mixing cavity has an inner surface including side walls arranged in the direction of oscillation for the mixing and upper and lower surfaces opposed to each other between the side walls, the analytical device includes a passage inlet for feeding the liquid from the mixing cavity to the measurement spots, the passage inlet being formed near one of the side walls arranged in the direction of oscillation for the mixing in the mixing cavity, and the mixing cavity includes a bending section formed at a point of the other side wall such that a distance between the side walls increases toward the inner periphery of the analytical device.

An analytical device of the present invention is an analytical device having a microchannel structure in which a first liquid and a second liquid are mixed in a mixing cavity and transferred to measurement cells by a centrifugal force, the analytical device being used for reading that accesses the liquid in the measurement cells, wherein the mixing cavity has an inner surface including side walls arranged in the direction of oscillation for the mixing and upper and lower surfaces opposed to each other between the side walls, the analytical device includes a passage inlet for feeding the liquid from the mixing cavity to the measurement spots, the passage inlet being formed near one of the wall surfaces of the upper and lower surfaces, and the mixing cavity includes: a level difference on the other wall surface of the upper and lower surfaces of the mixing cavity such that an inner gap is larger than an outer gap in the mixing cavity; and a bending section formed at a point of the other side wall such that a distance between the side walls increases toward the inner periphery of the analytical device.

Preferably, the analytical device of the present invention includes: a passage outlet for feeding the first liquid to the mixing cavity, the passage outlet being inserted inside the side walls of the mixing cavity; and a recessed section formed between the passage inlet and the passage outlet on the one wall surface of the upper and lower surfaces of the mixing cavity, except for a part continuing to the passage inlet, such that the recessed portion increases the gap of the mixing cavity. Further, it is preferable that the recessed section has a water-repellent inner surface.

Moreover, instead of the recessed section, a hydrophobic area having been given a water repellent finish may be formed in the same range as the recessed section.

Advantageous Effects of Invention

With this configuration, a passage inlet for feeding a liquid from a mixing cavity to the measurement spot is formed near one of the wall surfaces of upper and lower surfaces of the mixing cavity, the upper and lower surfaces being opposed to each other between side walls arranged in the direction of oscillation for mixing, a level difference is formed on the other wall surface of the upper and lower surfaces of the mixing cavity such that an inner gap is larger than an outer cap, and a bending section is formed on the other wall surface of the side walls of the mixing cavity such that a distance between the wall surfaces increases toward the inner periphery of an analytical device. Thus it is possible to reliably feed a solution from the mixing cavity to measurement cells.

Moreover, a passage outlet for supplying a sample component to the mixing cavity is inserted inside the side walls of the mixing cavity, a recessed section is formed on the one wall surface of the upper and lower surfaces of the mixing cavity, except for a part continuing to the passage inlet, such that the recessed section increases the gap of the mixing cavity, and a hydrophobic area having been given a water repellent finish is formed. Thus it is possible to prevent backflow of liquid and inflow of liquid afterward when performing an oscillating operation while stopping the rotations of the analytical device.

BRIEF DESCRIPTION OF DRAWINGS

FIG. 2 shows a front view and a bottom view of the analytical device according to the embodiment.

FIG. 19 shows a state diagram of the analytical device oscillated in step 6 of the embodiment, and a state diagram in which the turntable is rotationally driven in a clockwise direction to cause the sample liquid to flow into a measuring chamber and a reserving cavity.

FIG. 20 shows a state diagram of the analytical device oscillated in step 8 of the embodiment, and a state diagram in which the turntable is rotationally driven in the clockwise direction in step 9 to cause diluted plasma having reacted with the reagent of an operation cavity to flow into the separating cavity, and aggregates generated in the operation cavity are centrifugally separated by keeping a high-speed rotation.

FIG. 21 shows a state diagram in which the turntable is stopped, the diluted plasma flows into the measuring passage, and a fixed quantity of the diluted plasma is retained in the measuring passage in step 10 of the embodiment, and a state diagram in which the diluted plasma retained in the measuring passage flows into the measuring chamber in step 11.

FIG. 22 shows a state diagram in which a reaction of the diluted plasma in the measuring chamber and reagents is started in step 12 of the embodiment, and a state diagram of the agitation of the reagents and the diluted plasma in step 13.

FIG. 26 shows a plan view of a liquid level state of a mixing cavity before the oscillation of an analytical device according to a first example of the embodiment, a plan view of a liquid level state of the mixing cavity after oscillation, and a B-B sectional view of the mixing cavity.

DESCRIPTION OF EMBODIMENTS

FIGS. 1 to 6 show an analytical device of the present invention.

Figure 1:
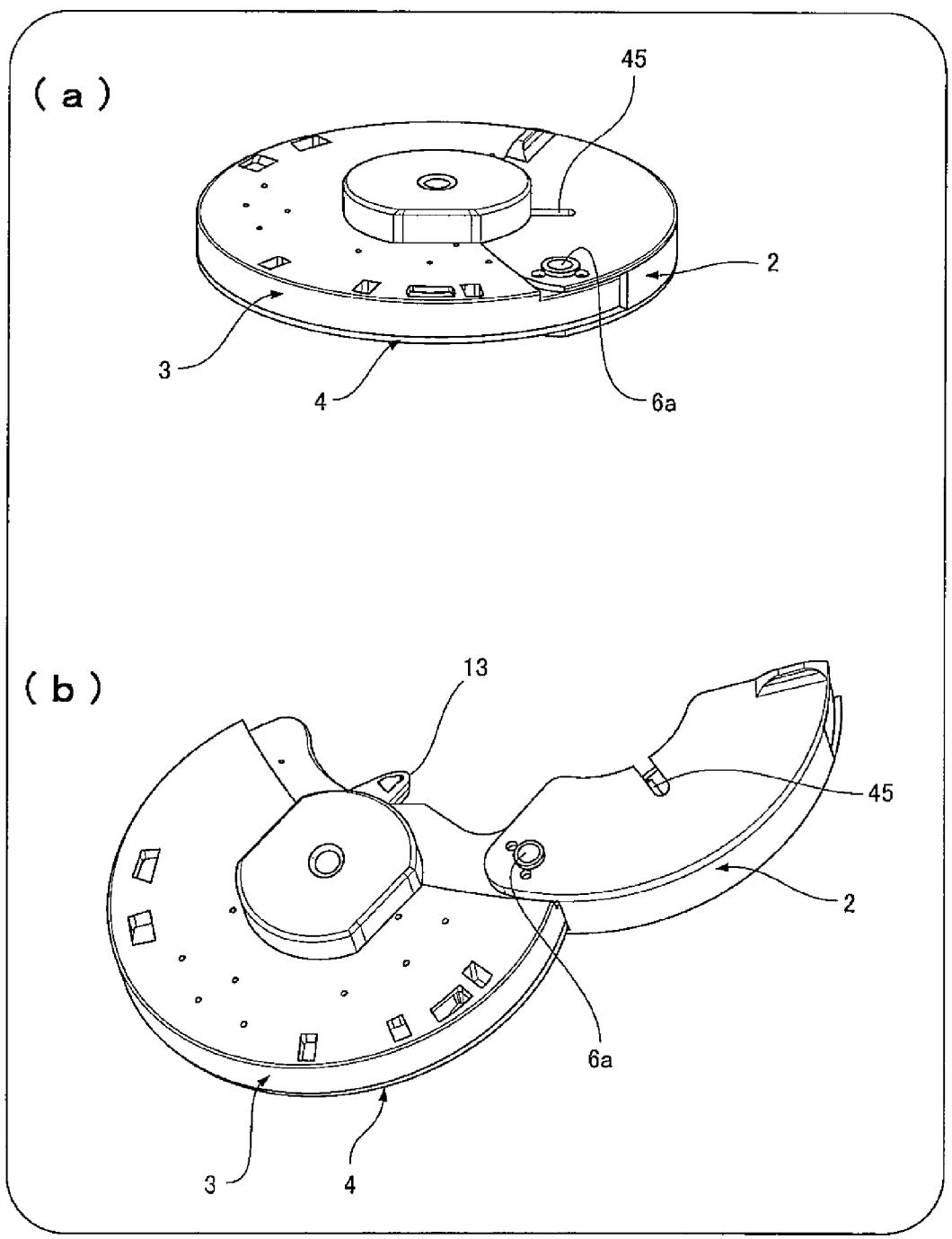
FIG. 1 is a perspective view showing an analytical device with an opened and closed protective cap according to an embodiment of the present invention.
Figure 3:
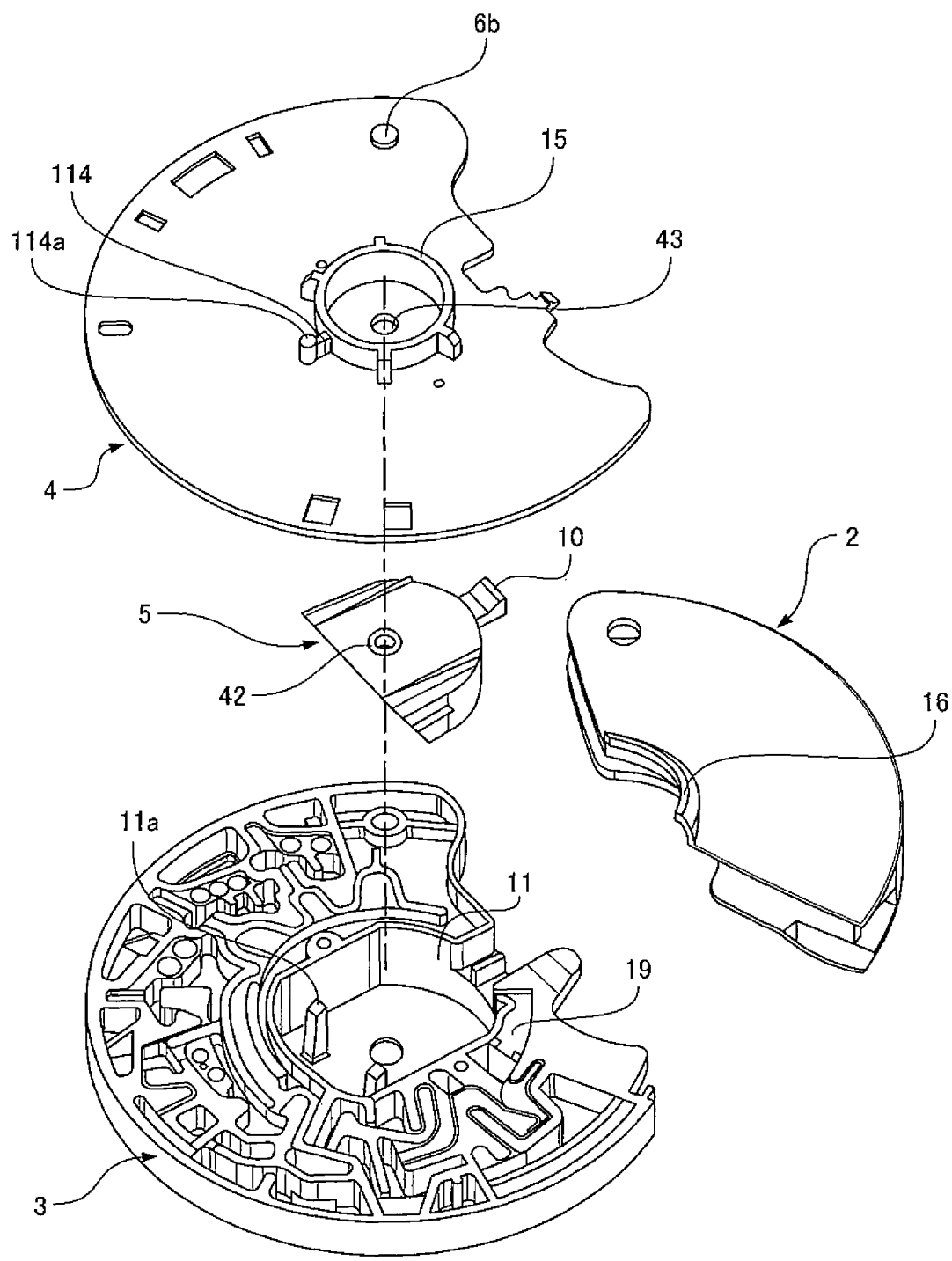
FIG. 3 is an exploded perspective view showing the analytical device according to the embodiment.

FIGS. 1(a) and 1(b) show an analytical device 1 with an opened and closed protective cap 2. FIGS. 2(a) and 2(b) are a front view and a bottom view of the analytical device 1. FIG. 3 is an exploded view of the analytical device 1 with the underside of FIG. 1(a) placed face up.

The analytical device 1 is made up of four components of a base substrate 3 having a microchannel structure formed on one surface of the base substrate 3, the microchannel structure having a minutely uneven surface, a cover substrate 4 covering the surface of the base substrate 3, a diluent container 5 for retaining a diluent, and the protective cap 2 for preventing splashes of a sample liquid.

On the bottom of the analytical device 1, that is, on the cover substrate 4, a rotary support section 15 is formed that protrudes on the bottom of the analytical device 1 and acts as a centering fitting part. On the inner periphery of the protective cap 2, a rotary support section 16 is formed. In the analytical device 1 with the protective cap 2 closed, the rotary support section 16 is formed in contact with the outer periphery of the rotary support section 15. On the cover substrate 4, a projecting section 114 is formed as a detent locking section having the proximal end connected to the rotary support section 15 and the other end extending to the outer periphery of the analytical device 1.

The base substrate 3 and the cover substrate 4 are joined to each other with the diluent container 5 or the like set in the base substrate 3 and the cover substrate 4, and the protective cap 2 is attached to the joined base substrate 3 and cover substrate 4.

The cover substrate 4 covers the openings of several recessed sections formed on the top surface of the base substrate 3, thereby forming multiple storage areas and the passages of the microchannel structure connecting the storage areas, which will be described later.

In necessary ones of the storage areas, reagents required for various analyses are set beforehand. One side of the protective cap 2 is pivotally supported such that the protective cap 2 can be opened and closed in engagement with shafts 6a and 6b formed on the base substrate 3 and the cover substrate 4. When a sample liquid to be inspected is blood, the passages of the microchannel structure receiving a capillary force have clearances of 50 μm to 300 μm.

The outline of an analyzing process using the analytical device 1 is that a sample liquid is dropped into the analytical device 1 in which the diluent has been set, at least a portion of the sample liquid is diluted with the diluent, and then measurement is conducted.

Figure 4:
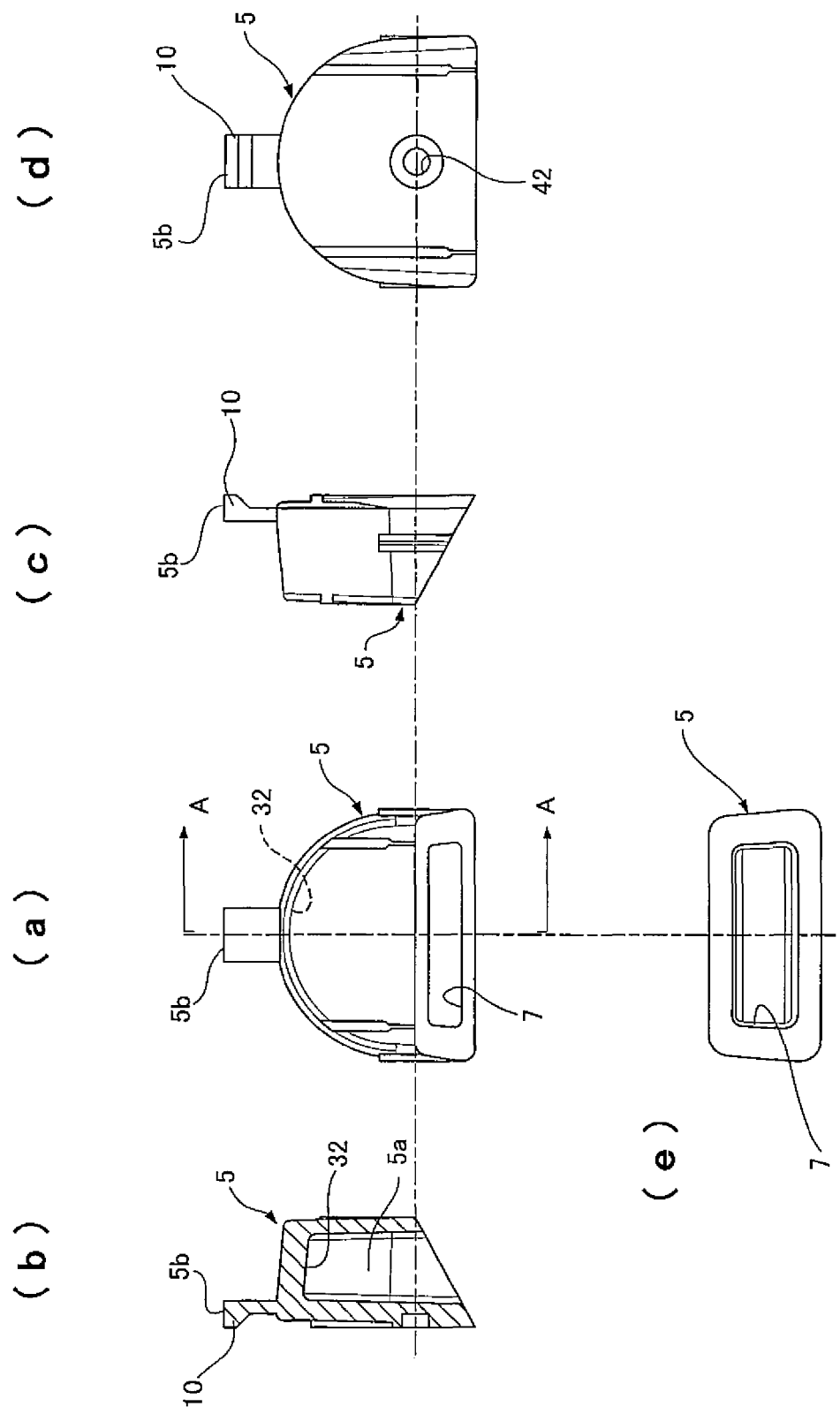
FIG. 4 shows a plan view, an A-A sectional view, a side view, a rear view, and a front view of a diluent container according to the embodiment.

FIG. 4 shows the shape of the diluent container 5.

FIG. 4(a) is a plan view, FIG. 4(b) is an A-A sectional view of FIG. 4(a), FIG. 4(c) is a side view, FIG. 4(d) is a rear view, and FIG. 4(e) is a front view taken from an opening 7. After an interior 5a of the diluent container 5 is filled with a diluent 8 as shown in FIG. 6(a), the opening 7 is enclosed with an aluminum seal 9 serving as a sealing member. On the opposite side of the diluent container 5 from the opening 7, a latch section 10 is formed. The diluent container 5 is set in a diluent container storage part 11 formed between the base substrate 3 and the cover substrate 4, and is accommodated movably between a liquid retaining position shown in FIG. 6(a) and a liquid discharging position shown in FIG. 6(c).

Figure 5:
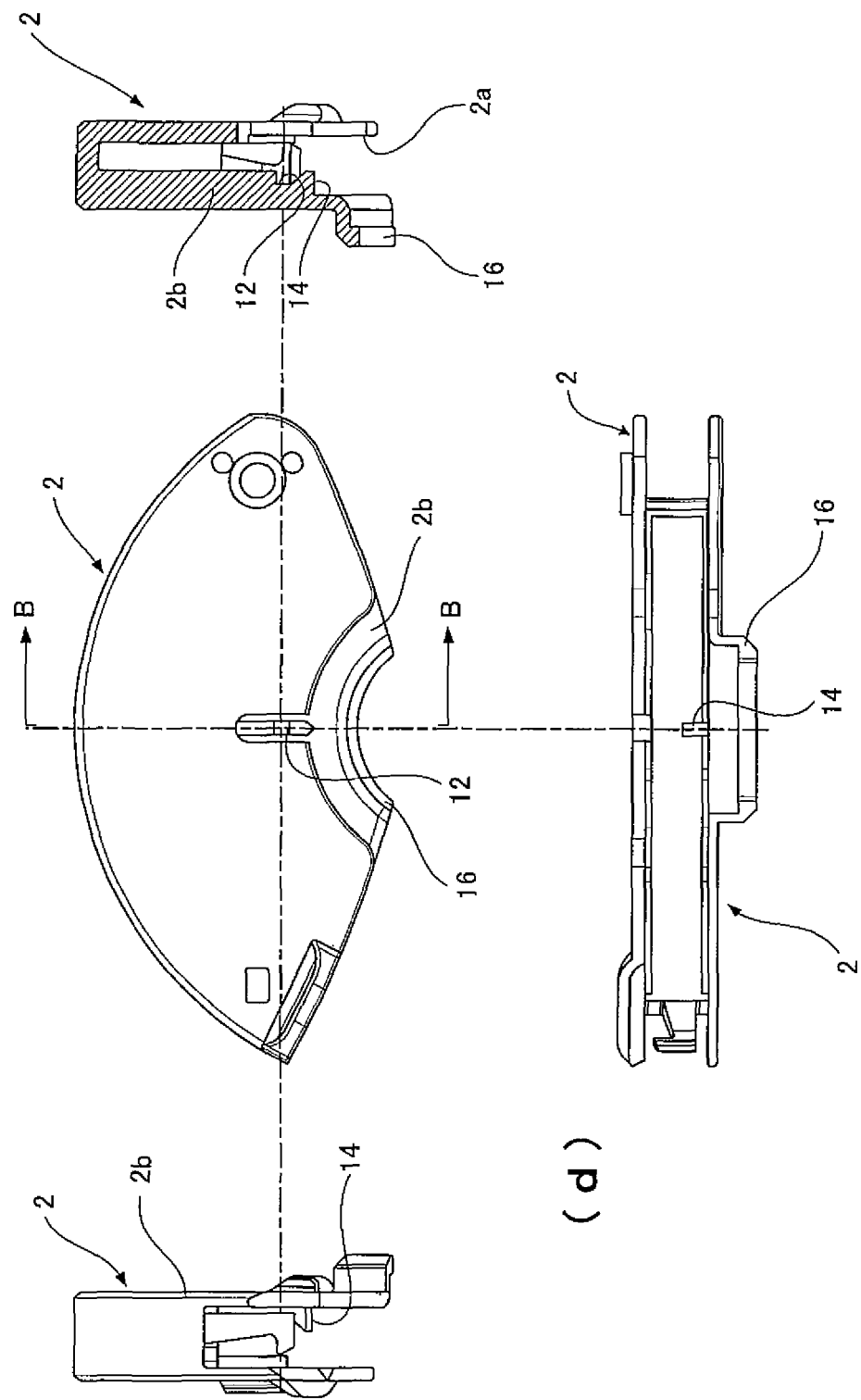
FIG. 5 shows a plan view, a side view, a B-B sectional view, and a front view of the protective cap according to the embodiment.
Figure 6:
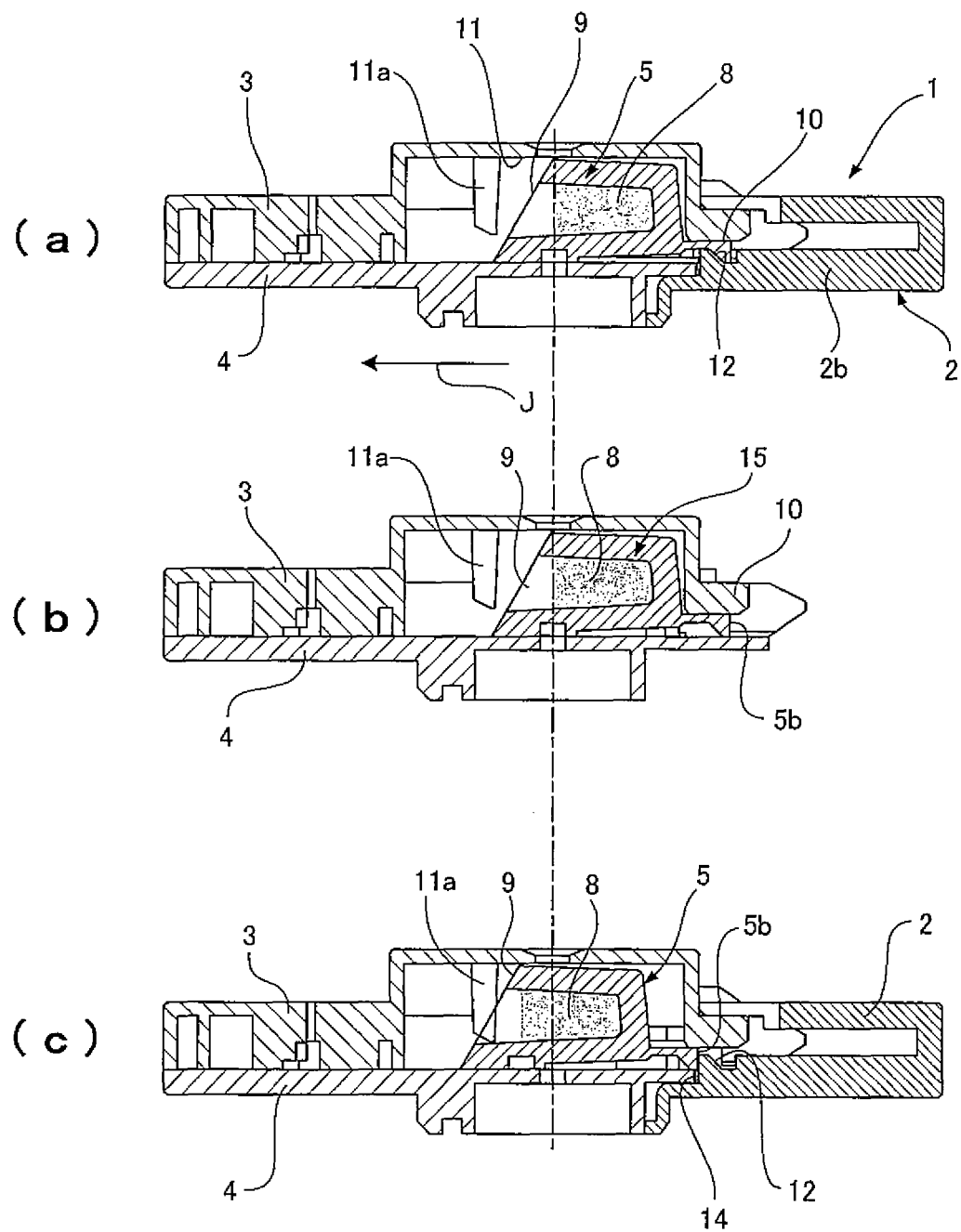
FIG. 6 shows sectional views of the closed diluent container, the opened protective cap, and a discharged diluent according to the embodiment.

FIG. 5 shows the shape of the protective cap 2.

FIG. 5(a) is a plan view, FIG. 5(b) is a side view, FIG. 5(c) is a B-B sectional view of FIG. 5(a), FIG. 5(d) is a rear view, and FIG. 5(e) is a front view taken from an opening 2a. In the protective cap 2, a locking groove 12 is formed. In the closed state of FIG. 1(a), the latch section 10 of the diluent container 5 can be engaged with the locking groove 12 as shown in FIG. 6(a).

FIG. 6(a) shows the analytical device 1 before use. In this state, the protective cap 2 is closed and the latch section 10 of the diluent container 5 is engaged with the locking groove 12 of the protective cap 2 to lock the diluent container 5 at the liquid retaining position, so that the diluent container 5 does not move in the direction of arrow J. The analytical device 1 in this state is supplied to a user.

When the sample liquid is dropped, the protective cap 2 is opened as shown in FIG. 1(b) against the engagement with the latch section 10 in FIG. 6(a). At this point, a bottom 2b of the protective cap 2 is elastically deformed with the locking groove 12 formed on the bottom 2b, thereby disengaging the latch section 10 of the diluent container 5 from the locking groove 12 of the protective cap 2 as shown in FIG. 6(b).

In this state, the sample liquid is dropped to an exposed inlet 13 of the analytical device 1 and then the protective cap 2 is closed. At this point, by closing the protective cap 2, a wall surface 14 forming the locking groove 12 comes into contact with a surface 5b of the latch section 10 of the diluent container 5 on the protective cap 2, and the wall surface 14 presses the diluent container 5 in the direction of arrow J (a direction along which the diluent container 5 comes close to the liquid discharging position). The diluent container storage part 11 has an opening rib 11a formed as a section projecting from the base substrate 3. When the diluent container 5 is pressed by the protective cap 2, the aluminum seal 9 provided on the inclined seal face of the opening 7 of the diluent container 5 is collided with and broken by the opening rib 11a as shown in FIG. 6(c).

Figure 7:
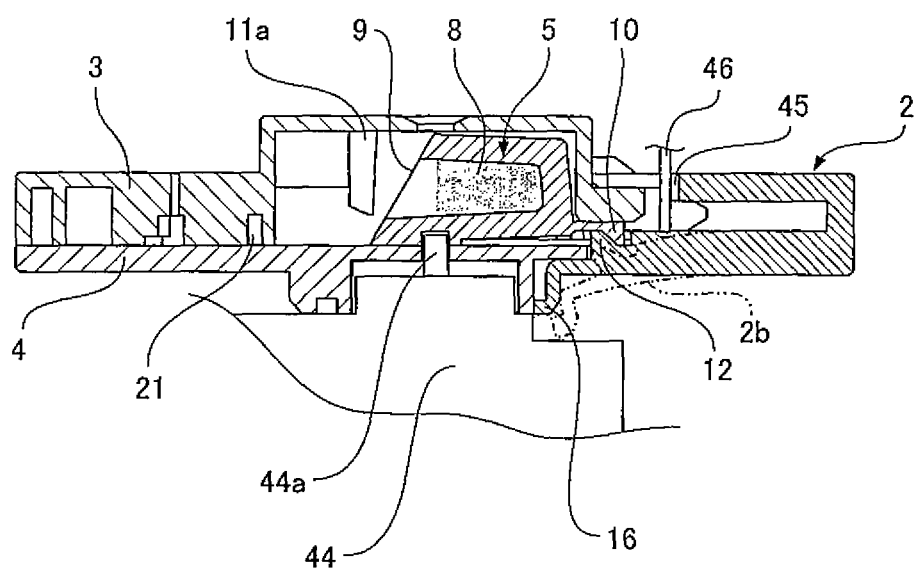
FIG. 7 is a sectional view showing a step of setting the analytical device in a shipping state according to the embodiment.

FIG. 7 shows a manufacturing process in which the analytical device 1 is set in the shipment state of FIG. 6(a). First, before the protective cap 2 is closed, a groove 42 (see FIGS. 3 and 4(d)) provided on the undersurface of the diluent container 5 and a hole 43 provided on the cover substrate 4 are aligned with each other, and a projecting section 44a of a locking member 44 is engaged with the groove 42 of the diluent container 5 through the hole 43 at the liquid retaining position. The projecting section 44a is provided separately from the base substrate 3 or the cover substrate 4. The diluent container 5 is set so as to be locked at the liquid retaining position. Further, from a notch 45 (see FIG. 1) formed on the top surface of the protective cap 2, a pressing member 46 is inserted and presses the bottom of the protective cap 2 to elastically deform the protective cap 2. In this state, the protective cap 2 is closed and then the pressing member 46 is removed, so that the analytical device 1 can be set in the state of FIG. 6(a).

The present embodiment described an example in which the groove 42 is provided on the undersurface of the diluent container 5. The groove 42 may be provided on the top surface of the diluent container 5 and the hole 43 may be provided on the base substrate 3 in alignment with the groove 42 such that the projecting section 44a of the locking member 44 is engaged with the groove 42.

Further, the locking groove 12 of the protective cap 2 is directly engaged with the latch section 10 of the diluent container 5 to lock the diluent container 5 at the liquid retaining position. The locking groove 12 of the protective cap 2 and the latch section 10 of the diluent container 5 may be indirectly engaged with each other to lock the diluent container 5 at the liquid retaining position.

Figure 8:
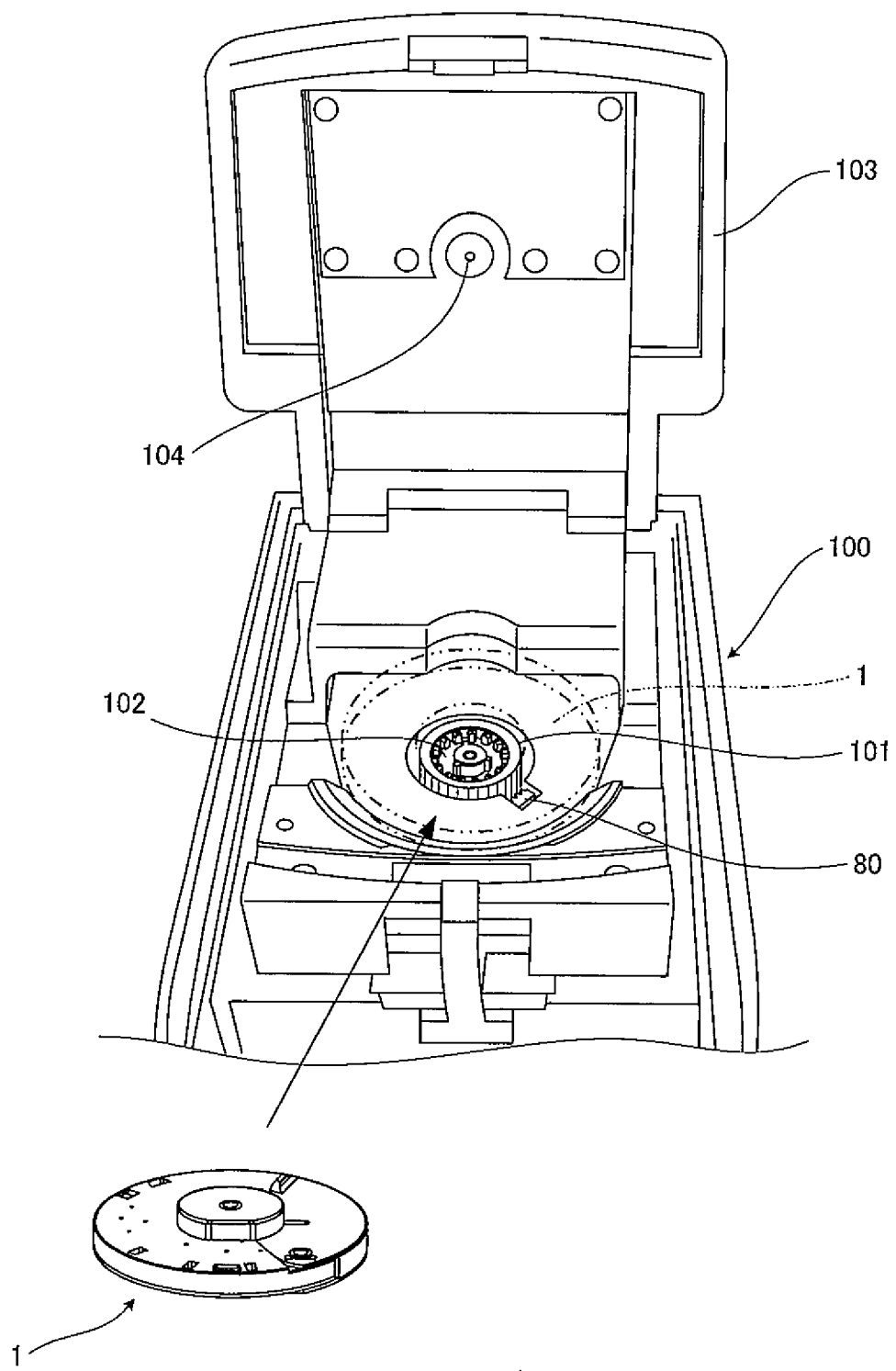
FIG. 8 is a perspective view showing the opened door of an analyzing apparatus according to the embodiment.
Figure 9:
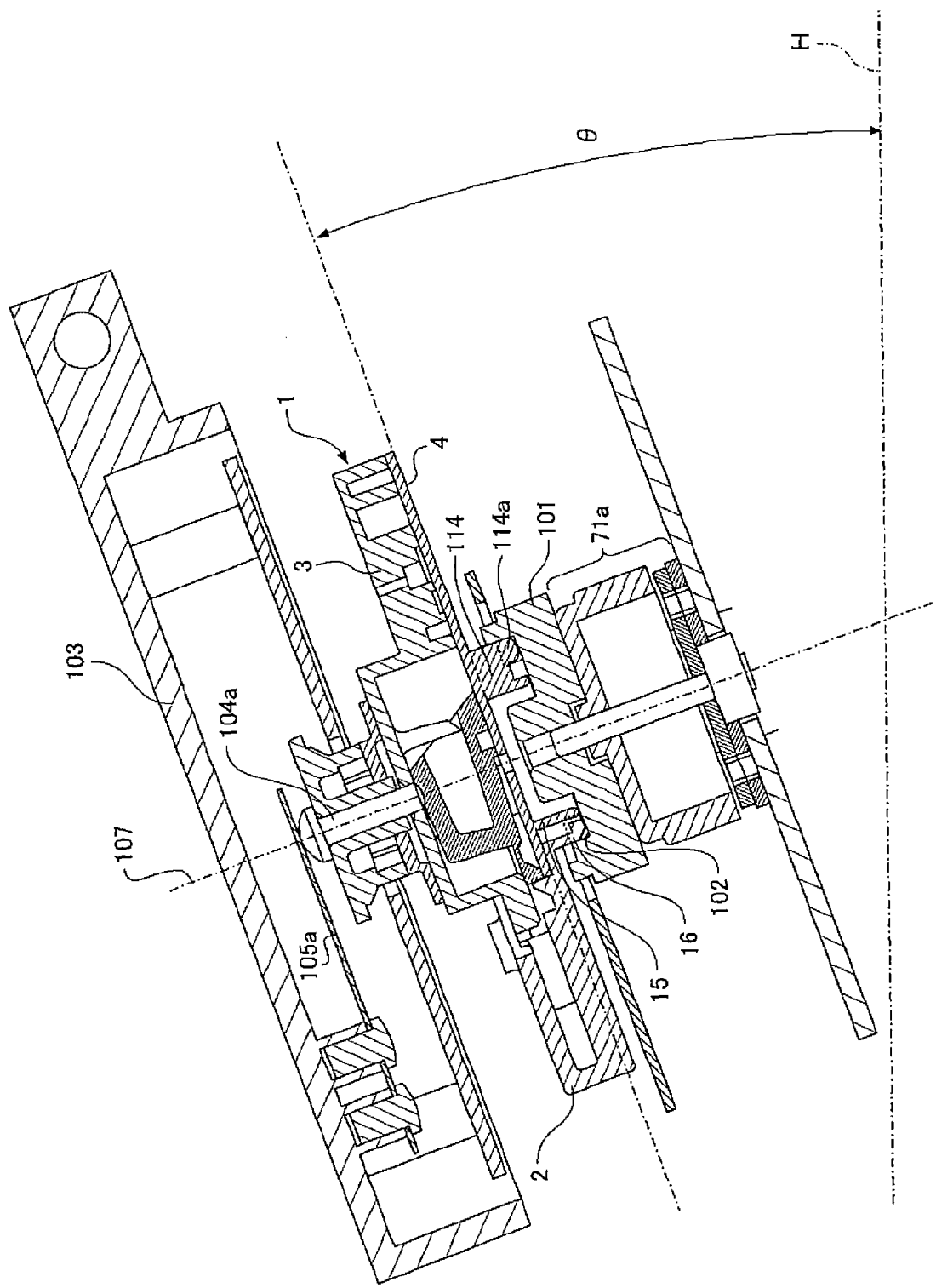
FIG. 9 is a sectional view showing the analyzing apparatus according to the embodiment.

As shown in FIGS. 8 and 9, the analytical device 1 is set on a turntable 101 of an analyzing apparatus 100.

In the present embodiment, the turntable 101 is attached around a rotation axis 107 tilted as shown in FIG. 9 and is tilted by an angle θ with respect to a horizontal line H. The direction of gravity to a solution in the analytical device 1 can be controlled according to the rotation stop position of the analytical device 1.

Figure 32:
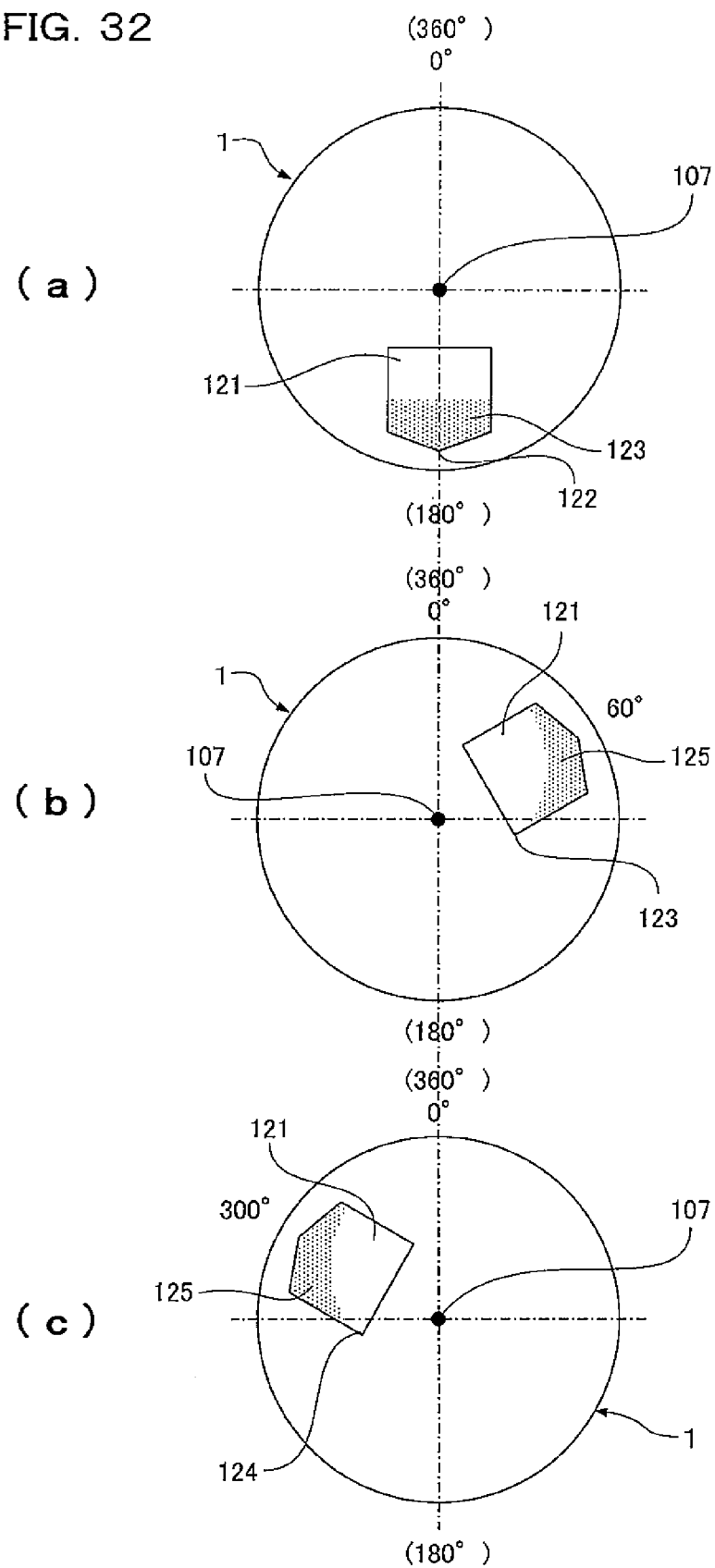
FIG. 32 shows a plan view of the analytical device when the turntable is stopped around 180° and a plan view of the analytical device when the turntable is stopped around 60° and 300°.

To be specific, when the analytical device 1 is stopped at the position of FIG. 32(a) (a position at about 180° when a position directly above the analytical device 1 in FIG. 32(a) is 0° (360°)), an underside 122 of an operation cavity 121 is directed downward when viewed from the front. Thus a force of gravity is applied to a solution 125 in the operation cavity 121 toward the outer periphery (underside 122) of the analytical device 1.

When the analytical device 1 is stopped at a position around 60° as shown in FIG. 32(b), an upper left side 123 of the operation cavity 121 is directed downward when viewed from the front. Thus a force of gravity is applied to the upper left of the solution 125 in the operation cavity 121. Similarly, at a position around 300° in FIG. 32(c), an upper right side 124 of the operation cavity 121 is directed downward when viewed from the front. Thus a force of gravity is applied to the upper right of the solution 125 in the operation cavity 121.

In this way, the rotation axis 107 is tilted and the analytical device 1 is stopped at any position, so that a force of gravity can be used as a driving force for transferring a solution in the analytical device 1 in a predetermined direction.

A force of gravity to a solution in the analytical device 1 can be set by adjusting the angle θ of the rotation axis 107. It is desirable to set a force of gravity depending on the relationship between a quantity of transferred liquid and the adhesion of applied liquid on a wall surface in the analytical device 1.

The angle θ is desirably set at 10° to 45°. When the angle θ is smaller than 10°, a force of gravity applied to the solution is so small that a driving force for transfer may not be obtained. When the angle θ is larger than 45°, a load applied to the rotation axis 107 may increase or the solution transferred by a centrifugal force may unexpectedly move under its own weight, resulting in an uncontrollable state.

On the top surface of the turntable 101, a circular groove 102 is formed. In a state in which the analytical device 1 is set on the turntable 101, the rotary support section 15 formed on the cover substrate 4 of the analytical device 1 and the rotary support section 16 formed on the protective cap 2 are engaged with the circular groove 102, so that the analytical device 1 is accommodated.

After the analytical device 1 is set on the turntable 101, a door 103 of the analyzing apparatus is closed before a rotation of the turntable 101, so that the set analytical device 1 is pressed to the turntable 101 by a clamper 104 provided on the door 103, at a position on the rotation axis of the turntable 101 by a biasing force of a spring 105a that serves as an urging member. The analytical device 1 rotates with the turntable 101 that is rotationally driven by a rotational drive unit 106. Reference numeral 107 denotes the rotation axis of the turntable 101.

Figure 10:
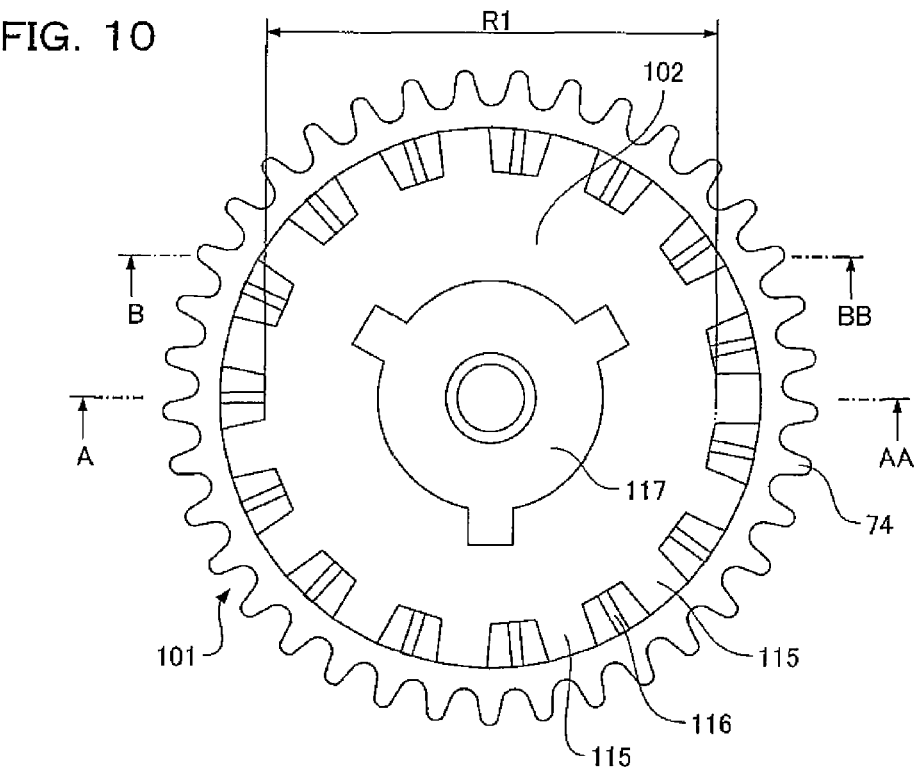
FIG. 10 is an enlarged plan view showing a turntable according to the embodiment.
Figure 11:
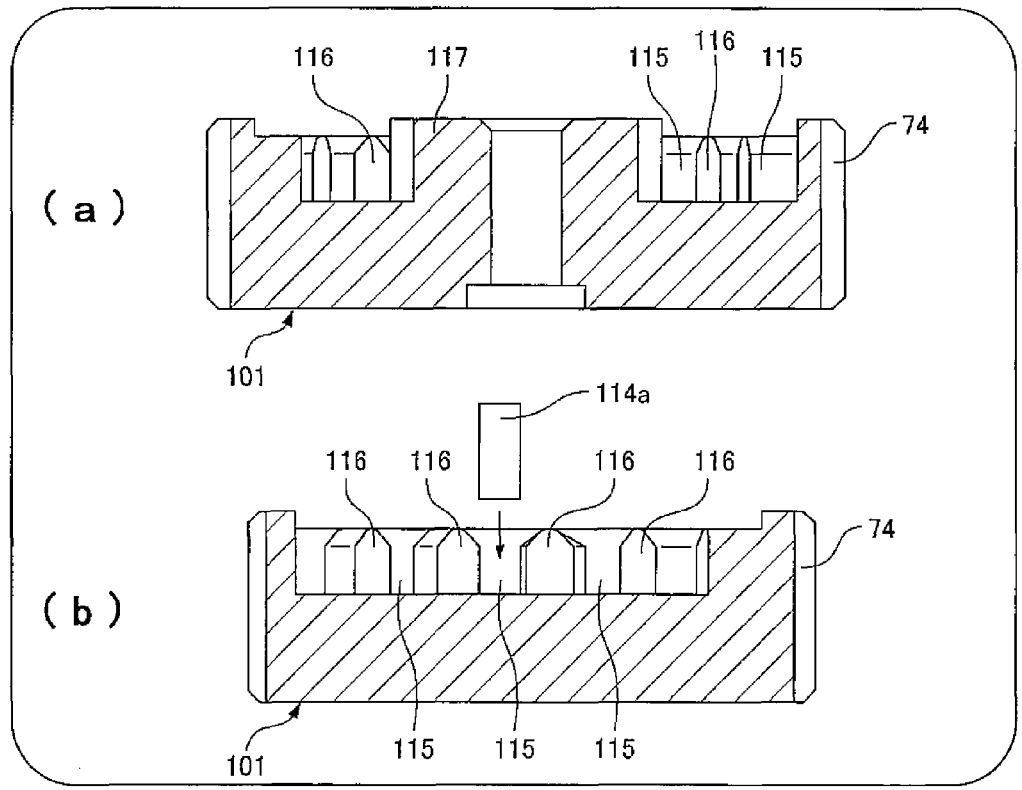
FIG. 11 shows an A-AA sectional view and a B-BB sectional view of the turntable according to the embodiment.

As shown in FIGS. 10 and 11(a), on the inner periphery of the circular groove 102 of the turntable 101, a plurality of grooves 115 are provided at regular intervals as detent locking sections on the turntable 101. FIG. 11(a) is an A-AA sectional view of FIG. 10 and FIG. 11(b) is a B-BB sectional view of FIG. 10. Partitions 116 between the grooves 115 of the turntable 101 have angular tops. Further, an internal diameter R1 of the partitions 116 between the grooves 115 is larger than an external diameter R2 of the rotary support section 15 that is provided at the center of the bottom of the analytical device 1 and is accommodated in the circular groove 102 of the turntable 101.

Figure 12:
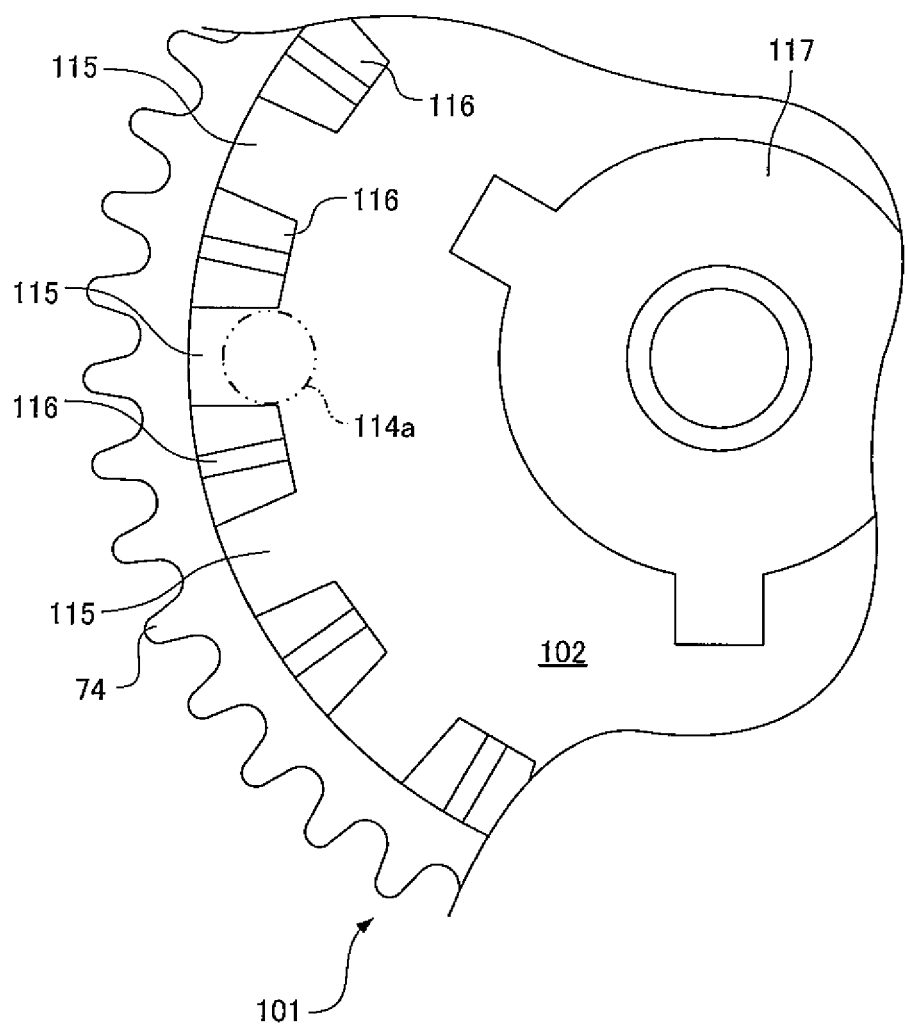
FIG. 12 is an enlarged plan view of the turntable, for the explanation of engagement between the turntable and a projecting section of the analytical device according to the embodiment.

With this configuration, when the analytical device 1 is set on the turntable 101, as shown in FIG. 9, a central projecting section 117 formed as a centering fitting section at the center of the circular groove 102 of the turntable 101 is located inside the rotary support section 15 of the analytical device 1, and the central projecting section 117 acts as a centering fitting section for centering the analytical device 1 and the turntable 101. At this point, as shown in FIGS. 9 and 12, an end 114a of the projecting section 114 of the analytical device 1 is engaged with any one of the grooves 115 formed at regular intervals on the inner periphery of the circular groove 102 of the turntable 101, so that the analytical device 1 does not slip in the circumferential direction of the turntable 101.

The protective cap 2 is attached to prevent the sample liquid applied around the inlet 13 from being splashed to the outside by a centrifugal force during analysis.

The components constituting the analytical device 1 are desirably made of resin materials achieving low material cost with high mass productivity. The analyzing apparatus 100 analyzes the sample liquid according to an optical measurement method for measuring light having passed through the analytical device 1. Thus the base substrate 3 and the cover substrate 4 are desirably made of transparent synthetic resins including PC, PMMA, AS, and MS.

The diluent container 5 is desirably made of crystalline synthetic resins such as PP and PE that have low moisture permeability. This is because the diluent container 5 has to contain the diluent 8 for a long time period. The protective cap 2 may be made of any materials as long as high moldability is obtained. Inexpensive resins such as PP, PE, and ABS are desirably used.

The base substrate 3 and the cover substrate 4 are desirably joined to each other according to a method hardly affecting the reaction activity of a reagent retained in the storage area. Thus methods such as ultrasonic welding and laser welding are desirable by which reactive gas and a solvent are hardly generated during joining.

On a part where a solution is transferred by a capillary force in a small clearance between the base substrate 3 and the cover substrate 4 that are joined to each other, hydrophilic treatment is performed to increase the capillary force. To be specific, hydrophilic treatment is performed using a hydrophilic polymer, a surface-active agent, and so on. In this case, hydrophilicity is a state in which a contact angle is less than 90° relative to water. More preferably, the contact angle is less than 40°.

Figure 13:
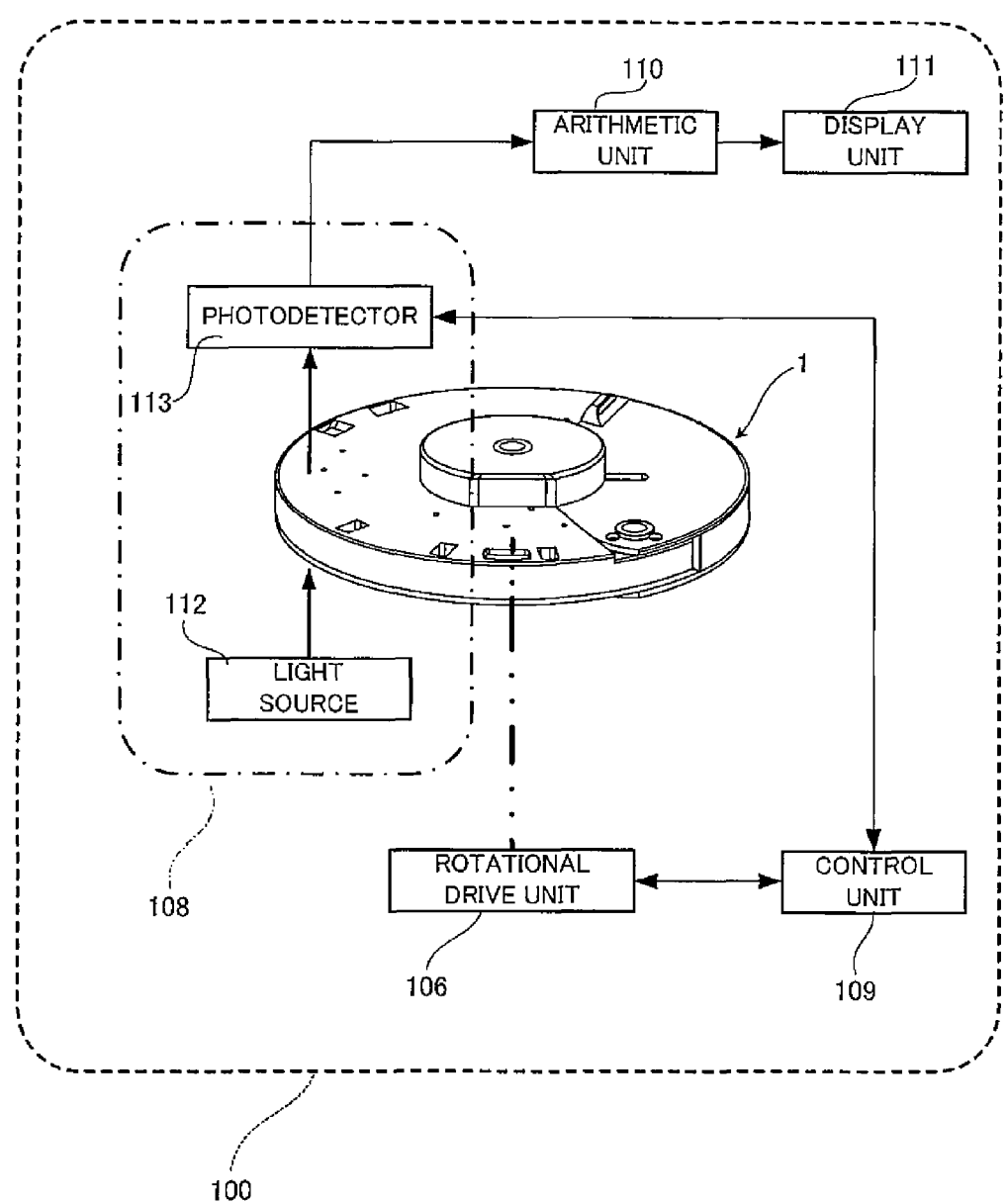
FIG. 13 is a structural diagram of the analyzing apparatus according to the embodiment.

FIG. 13 shows the configuration of the analyzing apparatus 100.

The analyzing apparatus 100 is made up of the rotational drive unit 106 for rotating the turntable 101; an optical measurement unit 108 for optically measuring a solution in the analytical device 1; a control unit 109 for controlling, e.g., the rotation speed and direction of the turntable 101 and the measurement timing of the optical measurement unit; an arithmetic unit 110 for calculating a measurement result by processing a signal obtained by the optical measurement unit 108; and a display unit 111 for displaying the result obtained by the arithmetic unit 110.

The rotational drive unit 106 can rotate the analytical device 1 through the turntable 101 about the rotation axis 107 in any direction at a predetermined rotation speed and can further oscillate the analytical device 1 such that the analytical device 1 laterally reciprocates at a predetermined stop position with respect to the rotation axis 107 with a predetermined amplitude range and a predetermined period.

The optical measurement unit 108 includes a light source 112 for emitting light of a specific wavelength to the measurement section of the analytical device 1; and a photodetector 113 for detecting the quantity of light having passed through the analytical device 1 out of the light emitted from the light source 112.

The analytical device 1 is rotationally driven by the turntable 101, and the sample liquid drawn into the analytical device 1 from the inlet 13 is transferred in the analytical device 1 by using a centrifugal force generated by rotating the analytical device 1 about the rotation axis 107 located inside the inlet 13 and the capillary force of a capillary tube channel provided in the analytical device 1. The microchannel structure of the analytical device 1 will be specifically described below along with an analyzing process.

Figure 14:
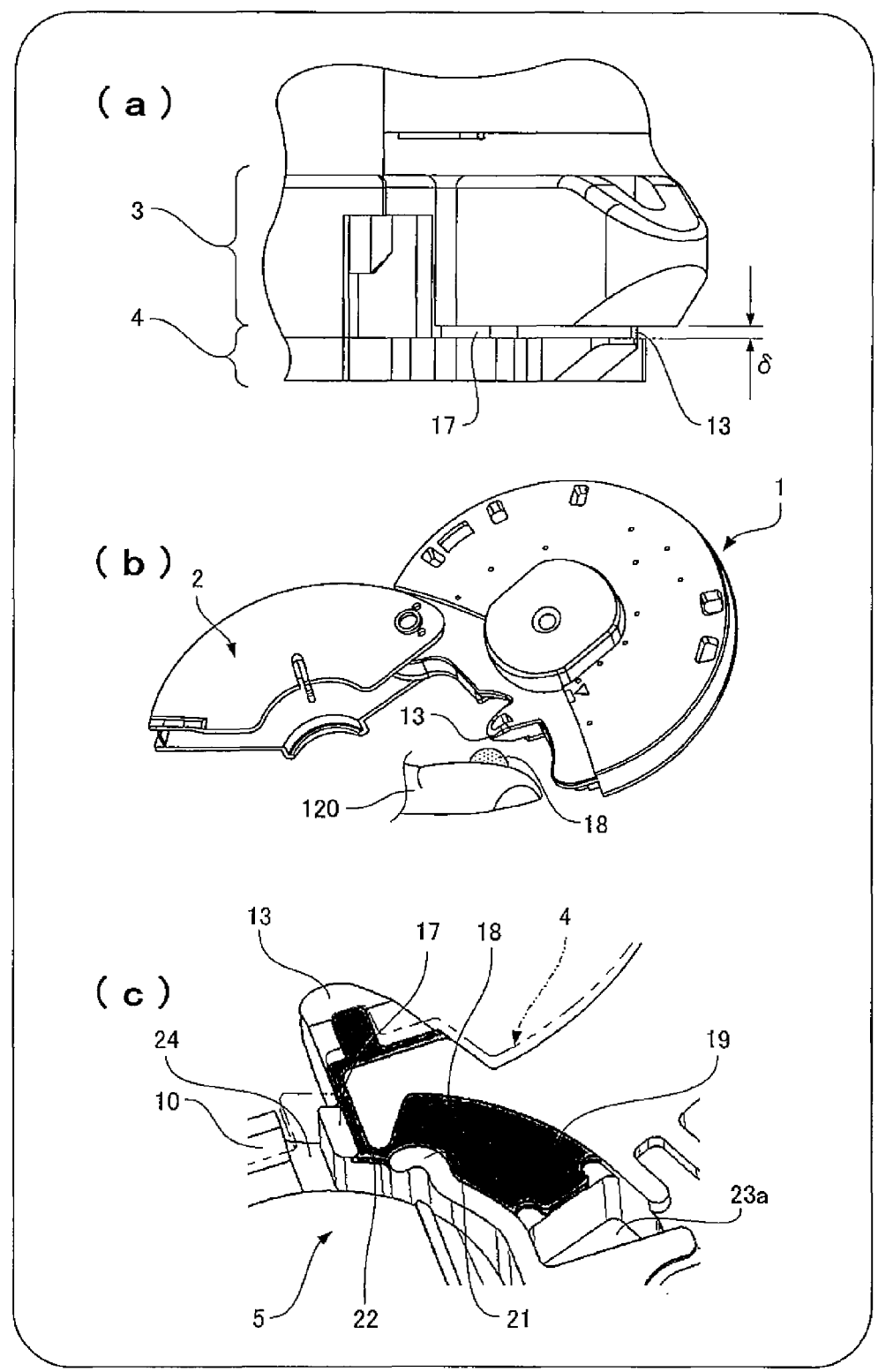
FIG. 14 shows an enlarged perspective view of a portion around the inlet of the analytical device, a perspective view showing that the protective cap is opened and a sample liquid is collected from a finger tip, and an enlarged perspective view of the microchannel structure of the analytical device that is viewed from the turntable through a cover substrate according to the embodiment.

FIG. 14 shows a part around the inlet 13 of the analytical device 1.

FIG. 14(a) is an enlarged view of the inlet 13 viewed from the outside of the analytical device 1. FIG. 14(b) shows that the protective cap 2 is opened and a sample liquid 18 is collected from a fingertip 120. FIG. 14(c) shows the microchannel structure viewed from the turntable 101 through the cover substrate 4.

The inlet 13 projects to the outer periphery of the analytical device 1 from the rotation axis 107 set in the analytical device 1 and the inlet 13 is connected to a capillary cavity 19 through a guide section 17 for receiving a capillary force with a small clearance 8 that is formed between the base substrate 3 and the cover substrate 4 so as to extend to the inner periphery of the analytical device 1. The capillary cavity 19 can retain a required quantity of the sample liquid 18 by a capillary force. With this configuration, the protective cap 2 is opened and the sample liquid 18 is directly applied to the inlet 13, so that the sample liquid applied around the inlet 13 is drawn into the analytical device 1 by the capillary force of the guide section 17.

On the guide section 17, the capillary cavity 19, and the connected section, a bending section 22 is formed that changes the direction of a passage with a recessed section 21 formed on the base substrate 3.

When viewed from the guide section 17, a receiving cavity 23a is formed behind the capillary cavity 19 such that the receiving cavity 23a has a clearance in which a capillary force is not applied. Partially on the sides of the capillary cavity 19, the bending section 22, and the guide section 17, a cavity 24 is formed that has one end connected to a separating cavity 23 and the other end opened to the atmosphere. By the effect of the cavity 24, the sample liquid collected from the inlet 13 passes through the guide section 17 and preferentially flows along the side walls of the capillary cavity 19 so as to avoid the cavity 24. Thus when air bubbles are entrained at the inlet 13, the air is discharged to the cavity 24 in a section where the guide section 17 is adjacent to the cavity 24, so that the sample liquid 18 can be collected without entraining air bubbles.

Figure 15:
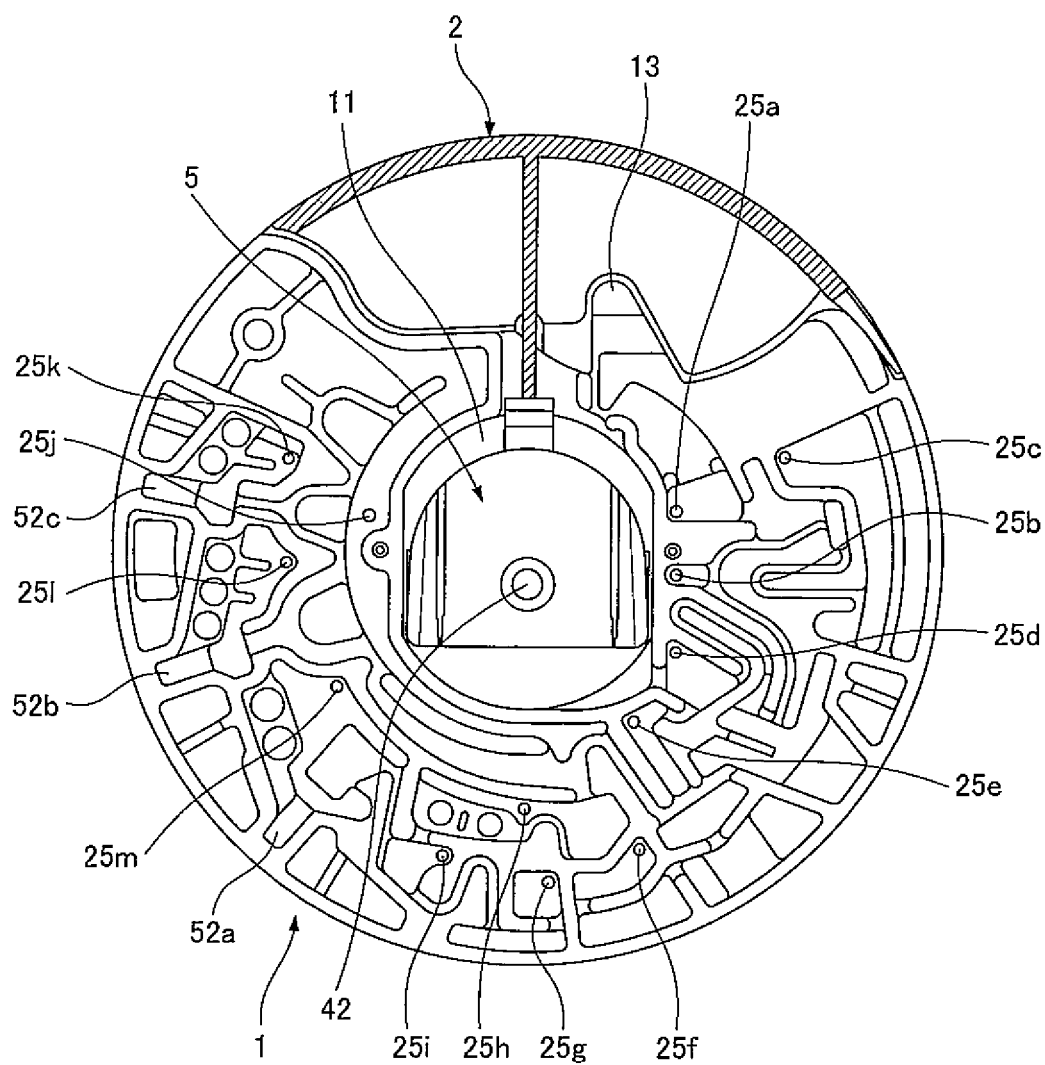
FIG. 15 is a state diagram showing a state before the analytical device containing the dropped sample liquid is set on the turntable according to the embodiment.

FIG. 15 shows a state before the analytical device 1 containing the dropped sample liquid 18 is set on the turntable 101 and is rotated thereon. At this point, as shown in FIG. 6(c), the aluminum seal 9 of the diluent container 5 has been collided with and broken by the opening rib 11a. Reference characters 25a to 25m denote air holes formed on the base substrate 3.

The following will describe the analyzing process along with the configuration of the control unit 109 that controls the operation of the rotational drive unit 106.

—Step 1—

Figure 16:
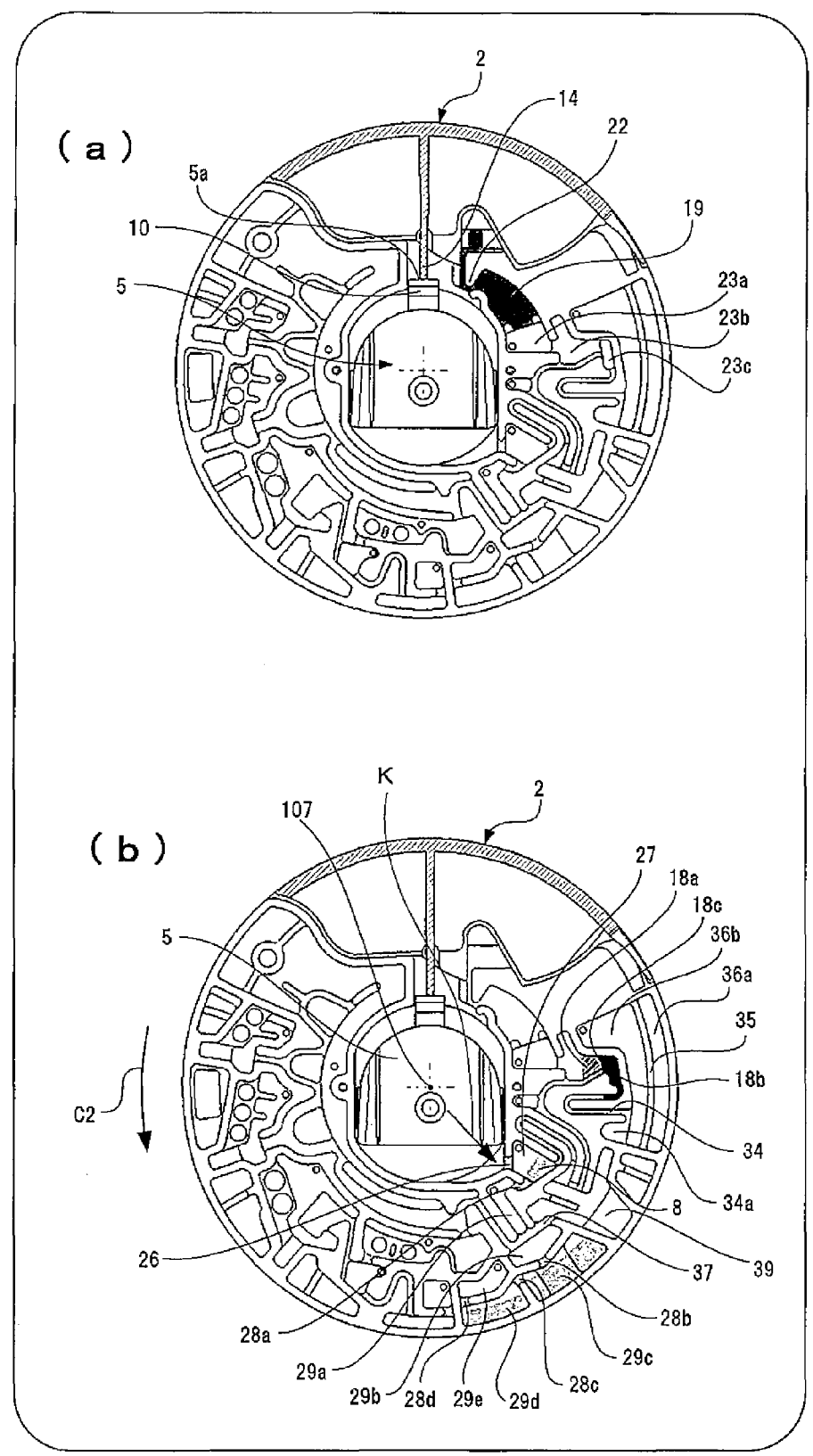
FIG. 16 shows a state diagram in which the analytical device retaining the sample liquid in a capillary cavity is set on the turntable with a broken aluminum seal of a diluent solution, and a state diagram showing that the analytical device is separated from the turntable according to the embodiment.

As shown in FIG. 16(a), the analytical device 1 in which a sample liquid to be inspected has been dropped into the inlet 13 is set on the turntable 101 in a state in which the sample liquid is retained in the capillary cavity 19 and the aluminum seal 9 of the diluent solution 5 has been broken.

—Step 2—

The door 103 is closed and then the turntable 101 is rotationally driven in a clockwise direction (direction C2), so that the retained sample liquid overflows at the position of the bending section 22. The sample liquid in the guide section 17 is discharged into the protective cap 2, and then as shown in FIG. 16(b), the sample liquid 18 in the capillary cavity 19 flows into separating cavities 23b and 23c through the receiving cavity 23a and is centrifugally separated into a plasma component 18a and a blood cell component 18b by the separating cavities 23b and 23c.

As shown in FIGS. 16(b) and 23(a), the diluent 8 from the diluent container 5 flows into a reserving cavity 27 through a discharging passage 26. When the diluent 8 having flowed into the reserving cavity 27 exceeds a predetermined quantity, an excessive quantity of the diluent 8 flows into an overflow cavity 29a through an overflow passage 28a, passes over a capillary tube channel 37, and flows into an overflow cavity 29c, which serves as a reference measuring chamber, through an overflow cavity 29b and an overflow passage 28b.

As in the reserving cavity 27, when the diluent having flowed into the overflow cavity 29c exceeds a predetermined quantity, an excessive quantity of the diluent flows into an overflow cavity 29d through an overflow passage 28c.

Figure 17:
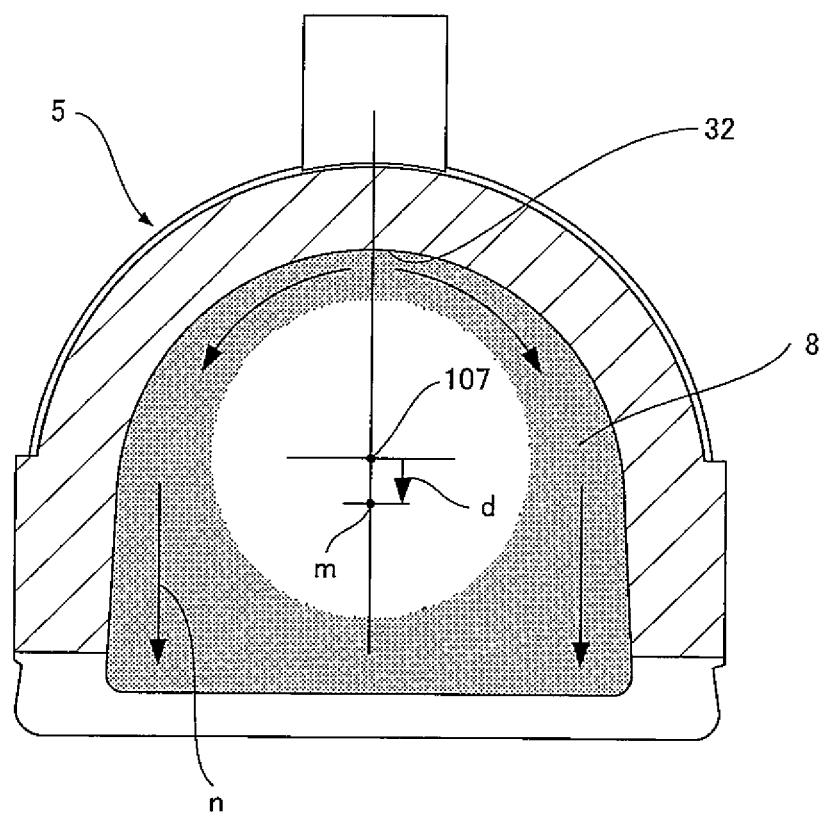
FIG. 17 is an enlarged sectional view for explaining the discharge of a liquid from the diluent container according to the embodiment.

As shown in FIGS. 4(*a*) and 4(*b*), the bottom of the diluent container 5 on the opposite side from the opening 7 sealed with the aluminum seal 9 is formed of a curved surface 32. At the liquid discharging position of the diluent container 5 in the state of FIG. 16(*b*), a center m of the curved surface 32 is offset, as shown in FIG. 17, by a distance d from the rotation axis 107 to the discharging passage 26. Thus the flow of the diluent 8 to the curved surface 32 is changed to a flow (arrow n) from the outside to the opening 7 along the curved surface 32, and then the diluent 8 is efficiently discharged to the diluent container storage part 11 from the opening 7 of the diluent container 5.

—Step 3—

Figure 18:
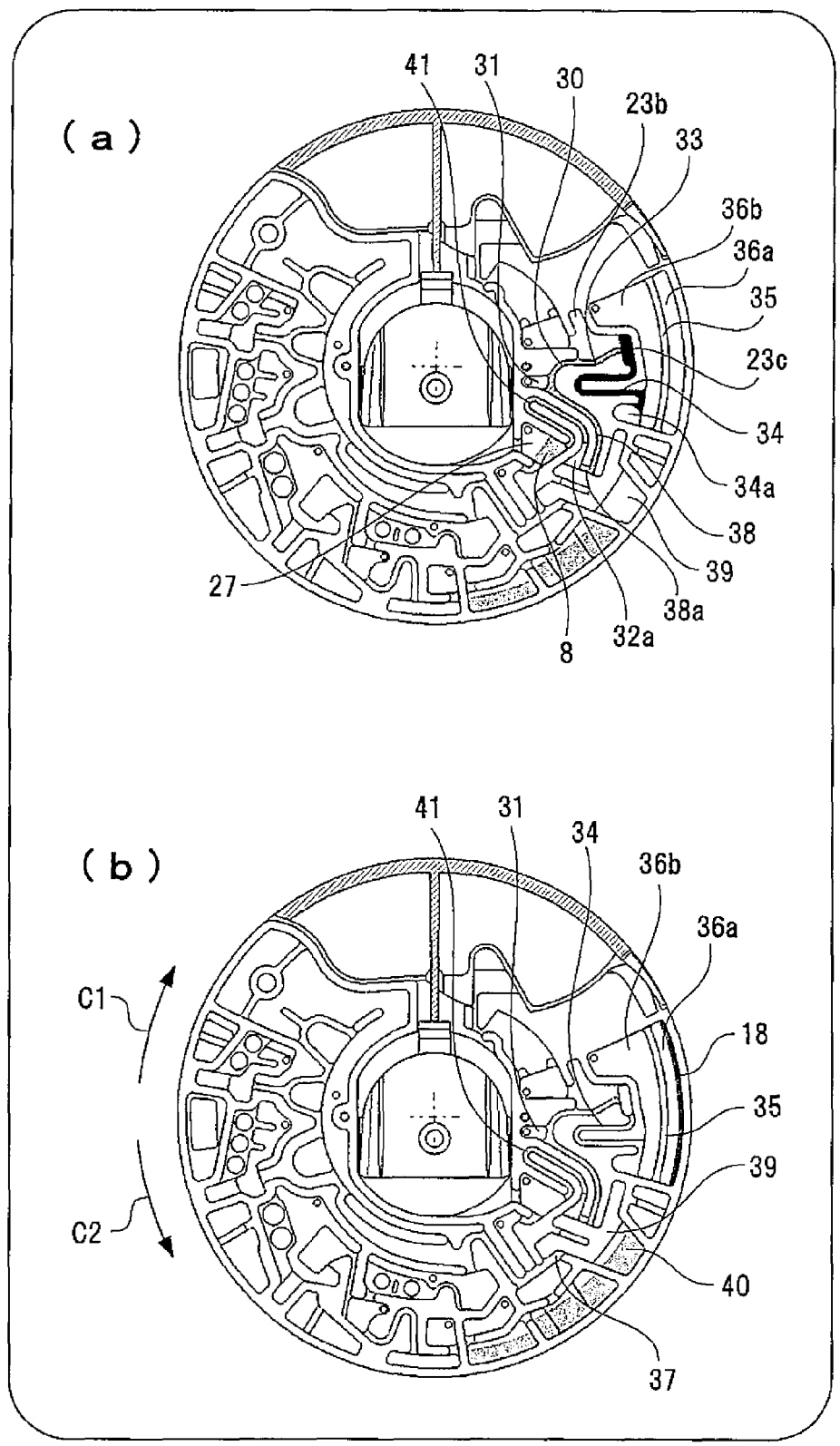
FIG. 18 shows a state diagram in which the sample liquid flows into a measuring passage from a separating cavity and a fixed quantity of the sample liquid is retained in the measuring passage in step 3, and a state diagram in which the sample liquid flows into a mixing cavity from the measuring passage in step 4 according to the embodiment.

Next, when the rotation of the turntable 101 is stopped, the plasma component 18a is sucked into a capillary cavity 33 formed on the wall surface of the separating cavity 23b and flows, as shown in FIG. 18(*a*), into a measuring passage 38 through a connecting passage 30 communicating with the capillary cavity 33, so that a fixed quantity of the plasma component 18a is retained.

In the present embodiment, a filling confirming area 38a is formed at the outlet of the measuring passage 38 so as to extend to the inner periphery of the analytical device 1. Before advancing to the subsequent process, the analytical device 1 is slowly rotated at around 100 rpm and the presence or absence of the plasma component 18a can be optically detected in a state in which the filling confirming area 38a retains the plasma component 18a. The filling confirming area 38a in the analytical device 1 has a rough inner surface that scatters light passing through the filling confirming area 38a. When the filling confirming area 38a is not filled with the plasma component 18a, the quantity of transmitted light decreases. When the filling confirming area 38a is filled with the plasma component 18a, the liquid is also applied to the minutely uneven surface. Thus the scattering of light is suppressed and the quantity of transmitted light increases. The presence or absence of the plasma component 18a can be detected by detecting a difference in light quantity.

The sample liquid in the separating cavities 23b and 23c is sucked into a connecting passage 34 that is siphon-shaped and connects the separating cavity 23c and an overflow cavity 36b. The diluent 8 is similarly sucked into a connecting passage 41 that is siphon-shaped and connects the reserving cavity 27 and a mixing cavity 39.

In this configuration, a flow preventing groove 32a at the outlet of the connecting passage 41 is formed to prevent the diluent 8 from flowing from the connecting passage 41 to the measuring passage 38. The flow preventing groove 32a is formed with a thickness of about 0.2 mm to 0.5 mm on the base substrate 3 and the cover substrate 4.

The capillary cavity 33 is formed from the outermost position of the separating cavity 23b to the inner periphery of the analytical device 1. In other words, the outermost position of the capillary cavity 33 is extended outside a separation interface 18c of the plasma component 18a and the blood cell component 18b in FIG. 16(*b*).

By setting the position of the outer periphery of the capillary cavity 33 thus, the outer end of the capillary cavity 33 is immersed in the plasma component 18a and the blood cell component 18b that have been separated in the separating cavity 23b. Since the plasma component 18a has a lower viscosity than the blood cell component 18b, the plasma component 18a is preferentially sucked by the capillary cavity 33. The plasma component 18a can be transferred to the measuring passage 38 through the connecting passage 30.

After the plasma component 18a is sucked, the blood cell component 18b is also sucked following the plasma component 18a. Thus the plasma component 18a can be replaced with the blood cell component 18b in the capillary cavity 33 and a path halfway to the connecting passage 30. When the measuring passage 38 is filled with the plasma component 18a, the transfer of the liquid is stopped also in the connecting passage 30 and the capillary cavity 33, so that the blood cell component 18b does not enter the measuring passage 38.

Hence, it is possible to minimize a loss of the transferred liquid as compared with the configuration of the related art, thereby reducing a quantity of the sample liquid required for measurement.

Figure 24:
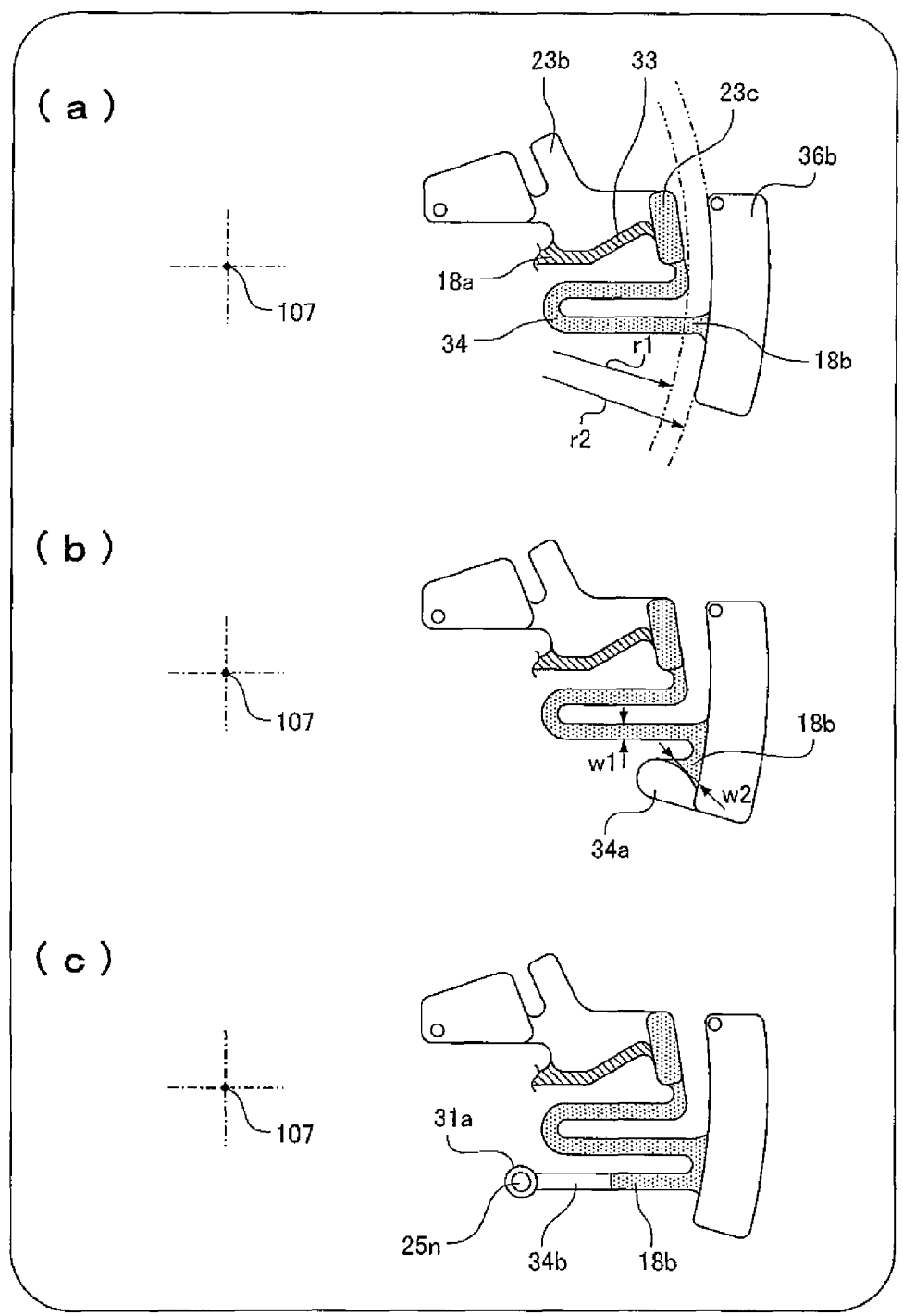
FIG. 24 shows an explanatory drawing of problems when the sample liquid remaining in the separating cavity is discharged to an overflow cavity, and a plan view of the principle part of the analytical device as an improvement example of the embodiment.
Figure 25:
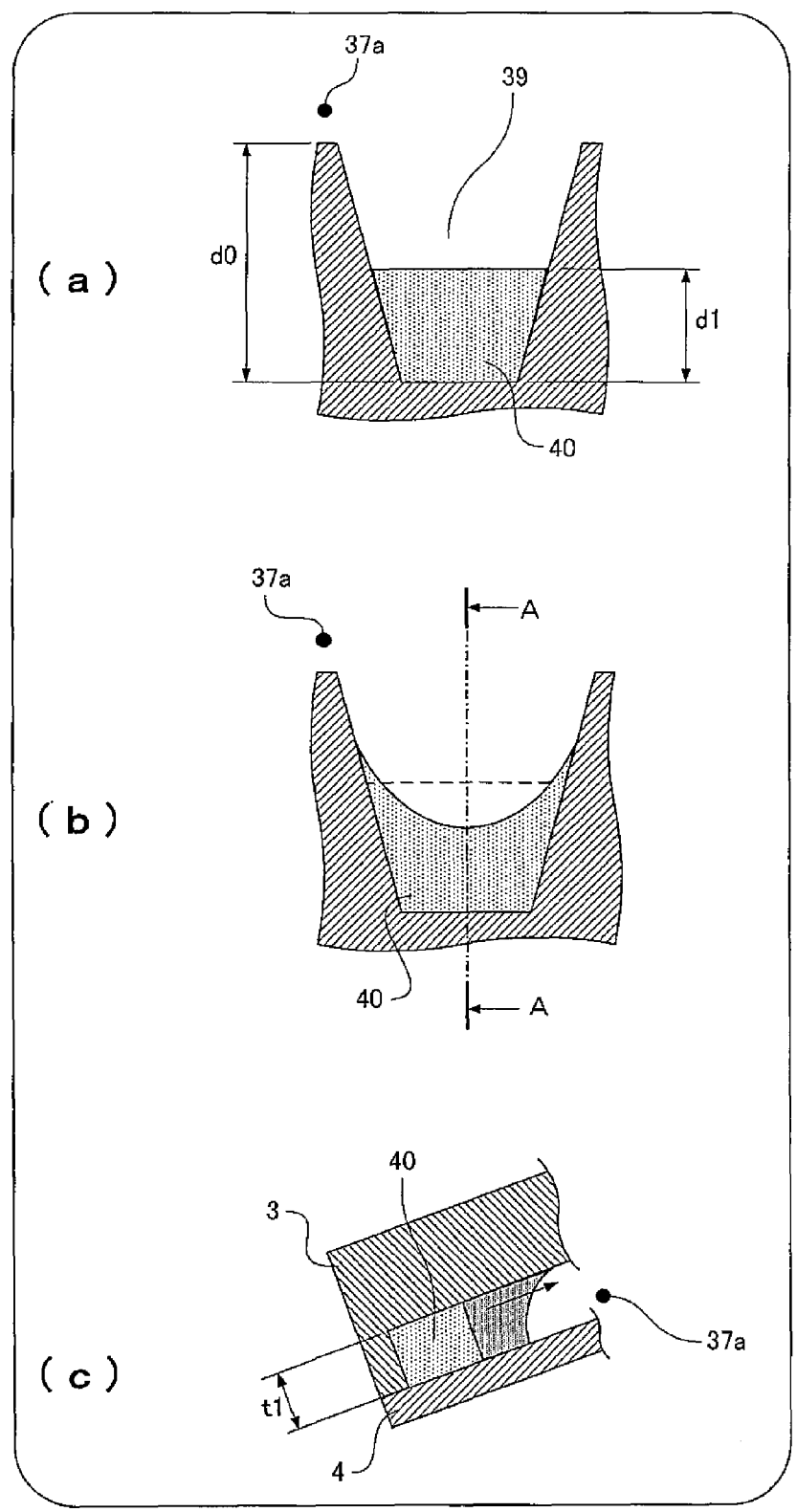
FIG. 25 shows a plan view of a liquid level state of the mixing cavity before oscillation for the explanation of the configuration of the mixing cavity and problems of a transferring method of a solution, a plan view of a liquid level state of the mixing cavity after oscillation, and an A-A sectional view of the mixing cavity.

FIG. 24 shows an enlarged view of the connecting passage 34 and a part around the connecting passage 34, which will be specifically described below.

In the related art, in order to prevent the sample liquid remaining in the separating cavities 23b and 23c from being sucked into the capillary cavity 33 and transferred to the subsequent process as shown in FIG. 24(*a*), the connecting passage 34 is provided that is siphon-shaped, is connected to the outermost position (r1) of the separating cavity 23c, and has a radial position (r2) at the outlet where r1<r2 is established. After the sample liquid is sucked into the connecting passage 34, the turntable 101 is rotated to discharge the sample liquid remaining in the separating cavities 23b and 23c to the overflow cavity 36b by a siphon action. However, when the sample liquid is blood, the blood cell component 18b passing through the connecting passage 34 is varied in transport speed among individuals. Thus it is necessary to start a rotation in the subsequent process in consideration of a time period until the blood cell component 18b reaches the outlet of the connecting passage 34. It has been found that the blood cell component 18b having early reached the outlet of the connecting passage 34 is clotted during a standby time before the subsequent process and then the blood cell component 18b clogs at the outlet of the connecting passage 34 and cannot be discharged at the start of a rotation in the subsequent process. In order to avoid this phenomenon, the position (r2) at the outlet of the connecting passage 34 may be further extended to the outer periphery of the analytical device 1 to prevent the blood cell component 18b from reaching the outlet of the connecting passage 34 and suppress the clotting of the blood cell component 18b. However, this configuration is not suitable for the size reduction of the analytical device 1.

In the present embodiment, as shown in FIG. 24(*b*), a liquid retaining section 34a is provided from the outlet of the connecting passage 34 in the circumferential direction and to the inner periphery of the analytical device 1. By providing the liquid retaining section 34a thus, the blood cell component 18b at the outlet of the connecting passage 34 flows into the liquid retaining section 34a. Thus the transfer of the blood cell component 18b is not stopped at the outlet of the connecting passage 34.

Since the width (w2) of the liquid retaining section 34a is larger than the width (w1) of the connecting passage 34, a surface tension is not applied in one direction on the liquid end of the blood cell component 18b, distributing a driving force. For this reason, the blood cell component 18b decreases in transport speed after flowing into the liquid retaining section 34a, so that variations in transport speed among individuals can be absorbed with a small area.

As shown in FIG. 24(*c*), a liquid retaining connecting passage 34b may be provided from the outlet of the connecting passage 34 to the inner periphery of the analytical device 1. Provided at the outlet of the liquid retaining connecting passage 34b are an opened-to-atmosphere cavity 31a and an air hole 25n communicating with the atmosphere in the cavity 31a.

This configuration can achieve the same effect as the configuration of FIG. 24(b).

—Step 4—

When the turntable 101 is rotationally driven in the clockwise direction (direction C2), as shown in FIG. 18(b), the plasma component 18a retained in the measuring passage 38 overflows at the position of the opened-to-atmosphere cavity 31a and only a fixed quantity of the plasma component 18a flows into the mixing cavity 39. The diluent 8 in the reserving cavity 27 also flows into the mixing cavity 39 through the siphon-shaped connecting passage 41.

The sample liquid 18 in the separating cavities 23b and 23c, the connecting passage 30, and the capillary cavity 33 flows into an overflow cavity 36a through the siphon-shaped connecting passage 34 and a backflow preventing passage 35.

—Step 5—

Next, the rotation of the turntable 101 is stopped, the analytical device 1 is set at the position of FIG. 18(b), and the turntable 101 is controlled at a frequency of 40 Hz to 80 Hz so as to oscillate the analytical device 1 by about ±1 mm, thereby agitating the diluent 8 transferred into the mixing cavity 39 and diluted plasma 40 to be measured, the diluted plasma 40 containing the plasma component 18a.

—Step 6—

After that, the analytical device 1 is set at the position of FIG. 19(a), the turntable 101 is controlled at a frequency of 80 Hz to 200 Hz so as to oscillate the analytical device 1 by about ±1 mm, and the diluted plasma 40 retained in the mixing cavity 39 is transferred to the inlet of the capillary tube channel 37 formed inside the liquid level of the diluted plasma 40.

The diluted plasma 40 transferred to the inlet of the capillary tube channel 37 is sucked into the capillary tube channel 37 by a capillary force and then is sequentially transferred to the capillary tube channel 37, measuring passages 47a, 47b, and 47c, and an overflow passage 47d.

Referring to FIGS. 25 to 31, the configuration of the mixing cavity 39 and a method of transferring a solution will be specifically described below according to the present embodiment.

FIG. 25(a) is a plan view showing a state of a liquid level in the mixing cavity 39 before oscillation. FIG. 25(b) is a plan view showing a state of the liquid level in the mixing cavity 39 after oscillation. FIG. 25(c) is an A-A sectional view of the mixing cavity 39 shown in FIG. 25(b).

The mixing cavity 39 is formed of inclined wall surfaces narrowing from the inner periphery toward the outermost position of the mixing cavity 39. The diluted plasma 40 can be retained at the liquid level (d1) and the capillary tube channel for transferring the diluted plasma 40 to the subsequent process has an inlet 37a at a position (d0) inside the liquid level d1.

The mixing cavity 39 operated in the present embodiment can contain a liquid of about several tens μl. Thus a large surface tension is applied to the wall surfaces of the mixing cavity 39 and the mixing cavity 39 is hardly affected by a force of gravity.

The following will describe a movement of the diluted plasma 40 retained in the mixing cavity 39 serving as an operation cavity, in the case where the analytical device 1 is oscillated with the operation cavity 121 positioned as shown in FIG. 25(a).

As shown in FIG. 25(b), the liquid level of the diluted plasma 40 in the mixing cavity 39 is laterally moved by an inertial force of oscillation, so that the diluted plasma 40 forms a liquid level that is pulled to the wall surfaces of the mixing cavity 39.

Therefore, the liquid level pulled to the wall surfaces is increased toward the inner periphery of the mixing cavity by repeatedly oscillating the analytical device 1, so that the diluted plasma 40 can be transferred to the inlet 37a of the capillary tube channel.

However, in the case where the mixing cavity 39 has a uniform thickness (t1), as shown in FIG. 25(c), the liquid level of the diluted plasma 40 increases along the top surface of the mixing cavity 39 (a surface on the base substrate 3), so that the diluted plasma 40 cannot reach the inlet 37a of the capillary tube channel provided near the bonded interface between the base substrate 3 and the cover substrate 4.

First Example

Therefore, in the present embodiment, a liquid level is controlled by the configuration of FIG. 26. FIG. 26(a) is a plan view showing a state of the liquid level in a mixing cavity 39 before oscillation. FIG. 26(b) is a plan view showing a state of the liquid level in the mixing cavity 39 after oscillation. FIG. 26(c) is a B-B sectional view of the mixing cavity 39 shown in FIG. 26(b).

In the mixing cavity 39, a level difference 39a is provided such that the mixing cavity 39 has a larger thickness at a position (d2) inside the liquid level (d1) of the diluted plasma 40 (t1<t2).

To be specific, the inner surface of the mixing cavity 39 is formed of a bottom 91 at the outermost position, side walls 39d and 39e arranged in a direction of oscillation for mixing, and opposed inner surfaces 92 and 93. The inner surface 92 of a base substrate 3 serves as the upper surface of the mixing cavity 39 and the inner surface 93 of a cover substrate 4 serves as the lower surface of the mixing cavity 39 between the side walls 39d and 39e. Further, an inlet 37a of a capillary tube channel 37 for feeding a liquid from the mixing cavity 39 to a measurement spot is formed near the inner surface of the cover substrate 4. Moreover, on the inner surface 92 of the base substrate 3, the level difference 39a is formed in a direction along which an inner gap t2 of the mixing cavity 39 is larger than an outer gap t1 of the mixing cavity 39.

By oscillating the analytical device 1 configured thus, an increase in liquid level on the wall surfaces provided along the gap direction of the mixing cavity 39 is suppressed by the level difference 39a provided on the substrate 3, that is, on the top surface of the mixing cavity 39, whereas the liquid level in contact with the cover substrate 4, that is, on the bottom of the mixing cavity 39 is increased toward the inner periphery with respect to the level difference 39a. This is because the level difference 39a is provided so as to apply a surface tension in a different direction from the extending direction of the liquid level. Thus the diluted plasma 40 can reach the inlet 37a of the capillary tube channel.

In step 5, however, it is necessary to retain a plasma component 18a and a diluent 8 in the mixing cavity 39 and reliably agitate the plasma component 18a and the diluent 8 by oscillation. Thus in order to prevent the liquid level from reaching the inlet 37a of the capillary tube channel during oscillation in step 5 and prevent suction into the capillary tube channel 37, it is necessary to provide a sufficient distance between the position (d0) of the inlet 37a of the capillary tube channel and a liquid level position (d1). Particularly, in the case of several tens μl of a liquid in the present embodiment, the liquid level is increased only by a short distance to the inner periphery by oscillation in the configuration of FIG. 26, so that the liquid level may not reach the inlet 37a of the capillary tube channel 37. Further, because of an insufficient distance to the inlet 37a of the capillary tube channel, the diluted plasma 40 may be sucked into the capillary tube channel 37 during agitation.

Second Example

Figure 27:
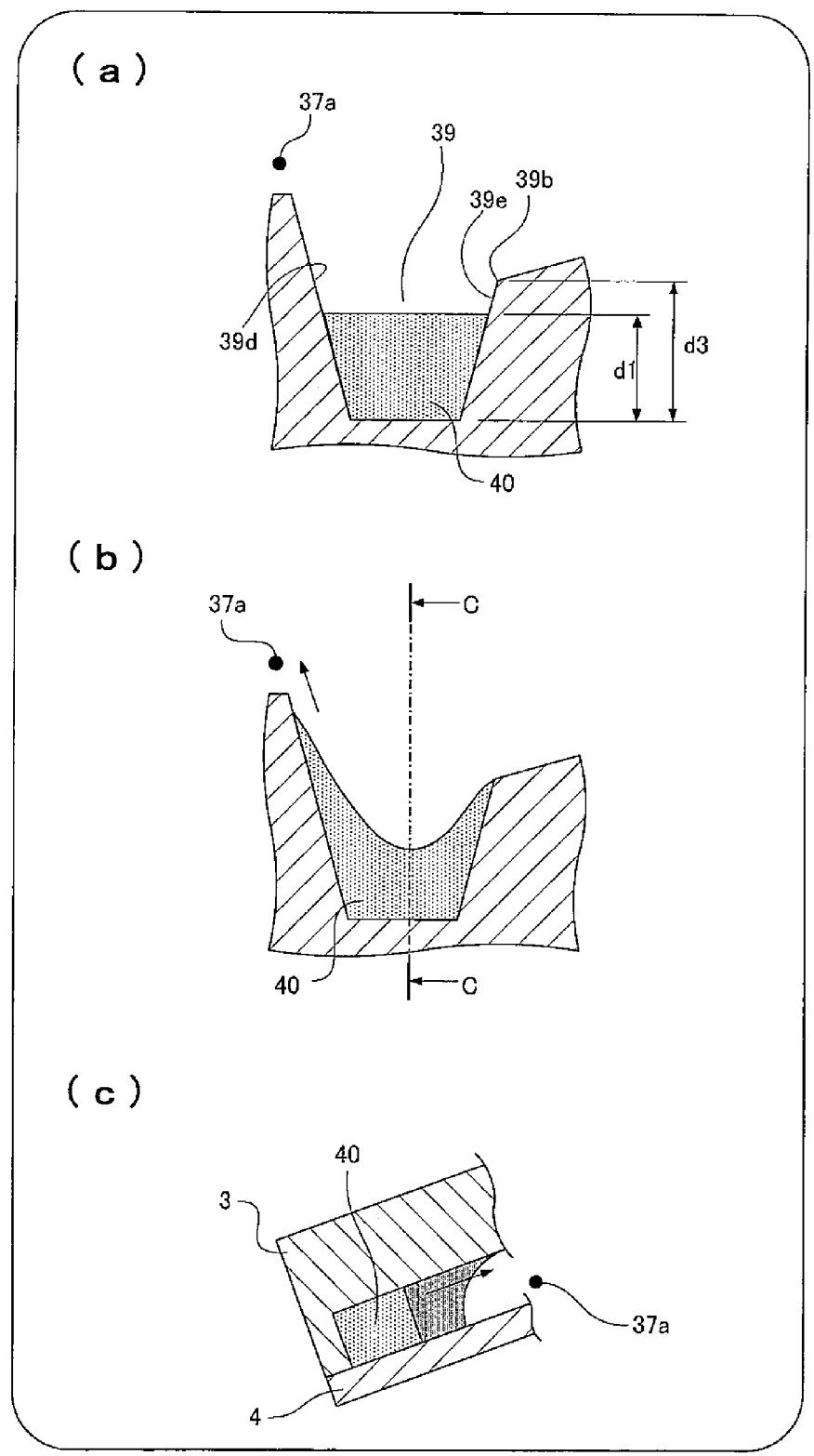
FIG. 27 shows a plan view of a liquid level state of a mixing cavity before the oscillation of an analytical device according to a second example of the embodiment, a plan view of a liquid level state of the mixing cavity after oscillation, and a C-C sectional view of the mixing cavity.

Referring to FIG. 27, the following will describe a configuration for increasing the extended distance of a liquid level only on one side of a mixing cavity 39 by oscillation. FIG. 27(a) is a plan view showing a state of a liquid level in the mixing cavity 39 before oscillation. FIG. 27(b) is a plan view showing a state of the liquid level in the mixing cavity 39 after oscillation. FIG. 27(c) is a C-C sectional view of the mixing cavity 39 shown in FIG. 27(b).

The mixing cavity 39 has a bending section 39b at a position (d3) inside the liquid level (d1) of diluted plasma 40, on a side wall 39e opposed to a side wall 39d on which an inlet 37a of a capillary tube channel is provided. The bending section 39b further expands the mixing cavity 39 toward the inner periphery of an analytical device 1.

By oscillating this configuration, on the side wall 39e opposed to the side wall 39d on which the inlet 37a of the capillary tube channel of the mixing cavity 39 is provided, an increase in the liquid level is suppressed by the bending section 39b provided on the wall surface, whereas on the wall surface on which the inlet 37a of the capillary tube channel is provided, the liquid level is further increased to the inner periphery. This is because the bending section 39b is provided to apply a surface tension in a different direction from the extending direction of the liquid level. Thus even when the inlet 37a of the capillary tube channel is sufficiently separated, the liquid level can reach the inlet 37a.

Third Example

Figure 28:
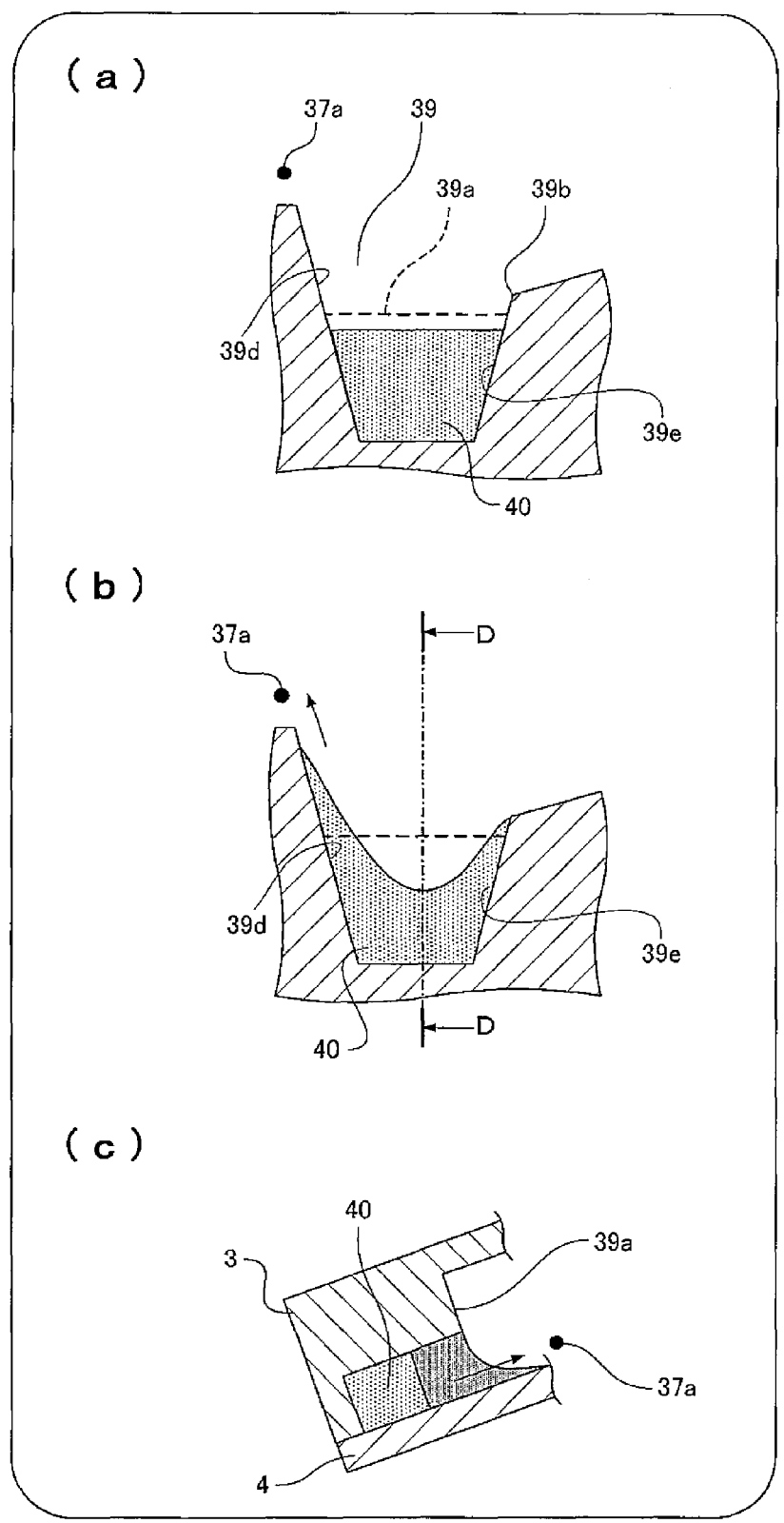
FIG. 28 shows a plan view of a liquid level state of a mixing cavity before the oscillation of an analytical device according to a third example of the embodiment, a plan view of a liquid level state of the mixing cavity after oscillation, and a D-D sectional view of the mixing cavity.
Figure 29:
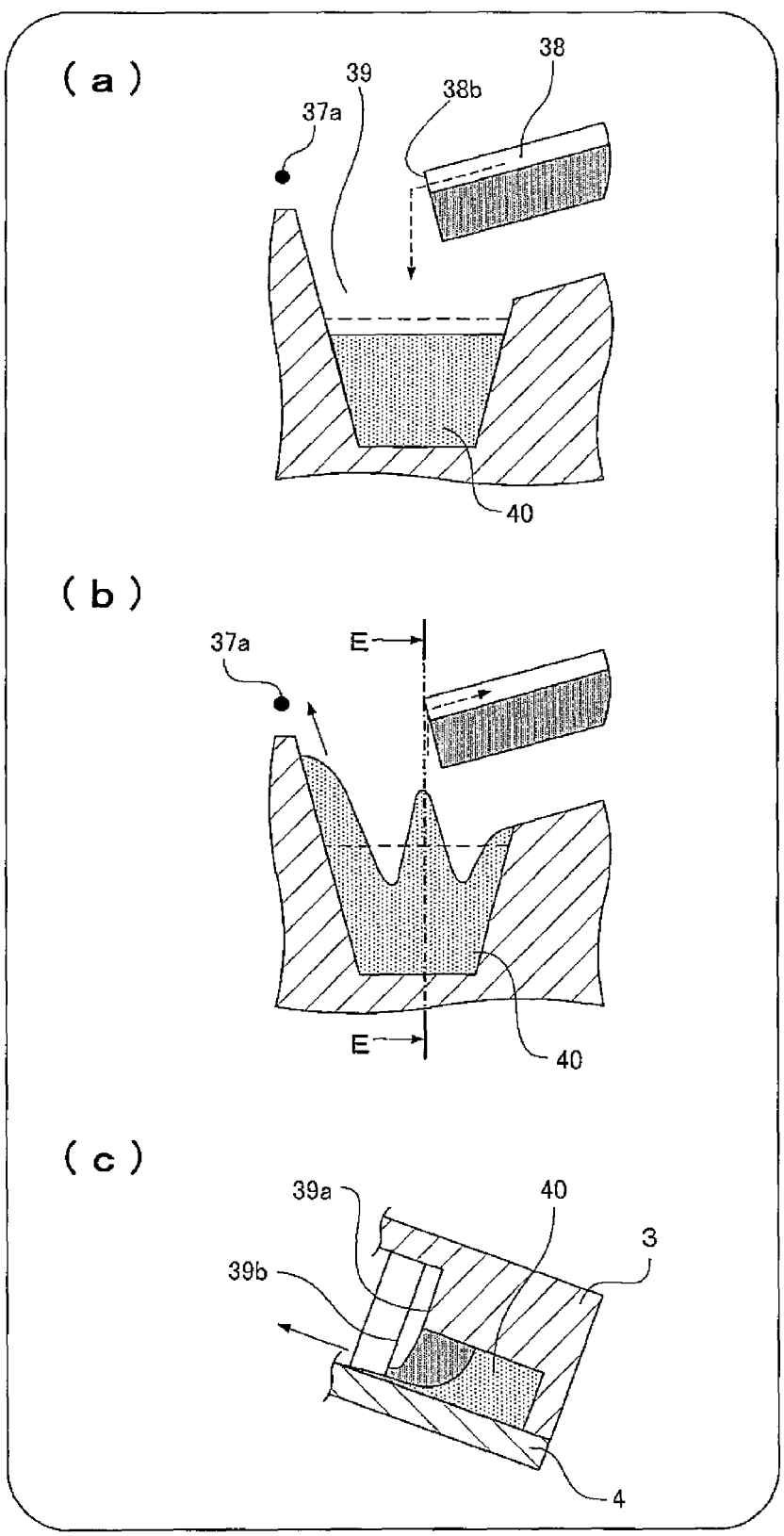
FIG. 29 shows a plan view of a liquid level state of the mixing cavity before oscillation, for the explanation of problems of the size reduction of the analytical device, a plan view of a liquid level state of the mixing cavity after oscillation, and an E-E sectional view of the mixing cavity.

In FIG. 28, the configurations of FIG. 26 and FIG. 27 are combined to control a liquid level. As shown in FIGS. 28(a) and 28(b), a bending section 39b is formed on a side wall 39e. As shown in FIG. 28(c), a step 39a is formed on a base substrate 3. The liquid level moves as illustrated in FIGS. 26 and 27.

Fourth Example

In order to further reduce the size of an analytical device 1, as shown in FIG. 29(a), the outlet of a measuring passage 38 may be formed near the liquid level of diluted plasma 40 retained in a mixing cavity 39.

A plasma component 18a retained in the measuring passage 38 is transferred to the mixing cavity 39 by a centrifugal force generated by a rotation of the analytical device 1. At this point, the plasma component 18a is transferred while moistening the surface of a cover substrate 4. The surface moistened once decreases in surface tension and thus a liquid easily spreads over the surface. Therefore, as shown in FIG. 29(b), the oscillated mixing cavity 39 may cause the diluted plasma 40 to spread to a path where the plasma component 18a has passed, reach the outlet of the measuring passage 38, and flow backward into the measuring passage 38.

Figure 30:
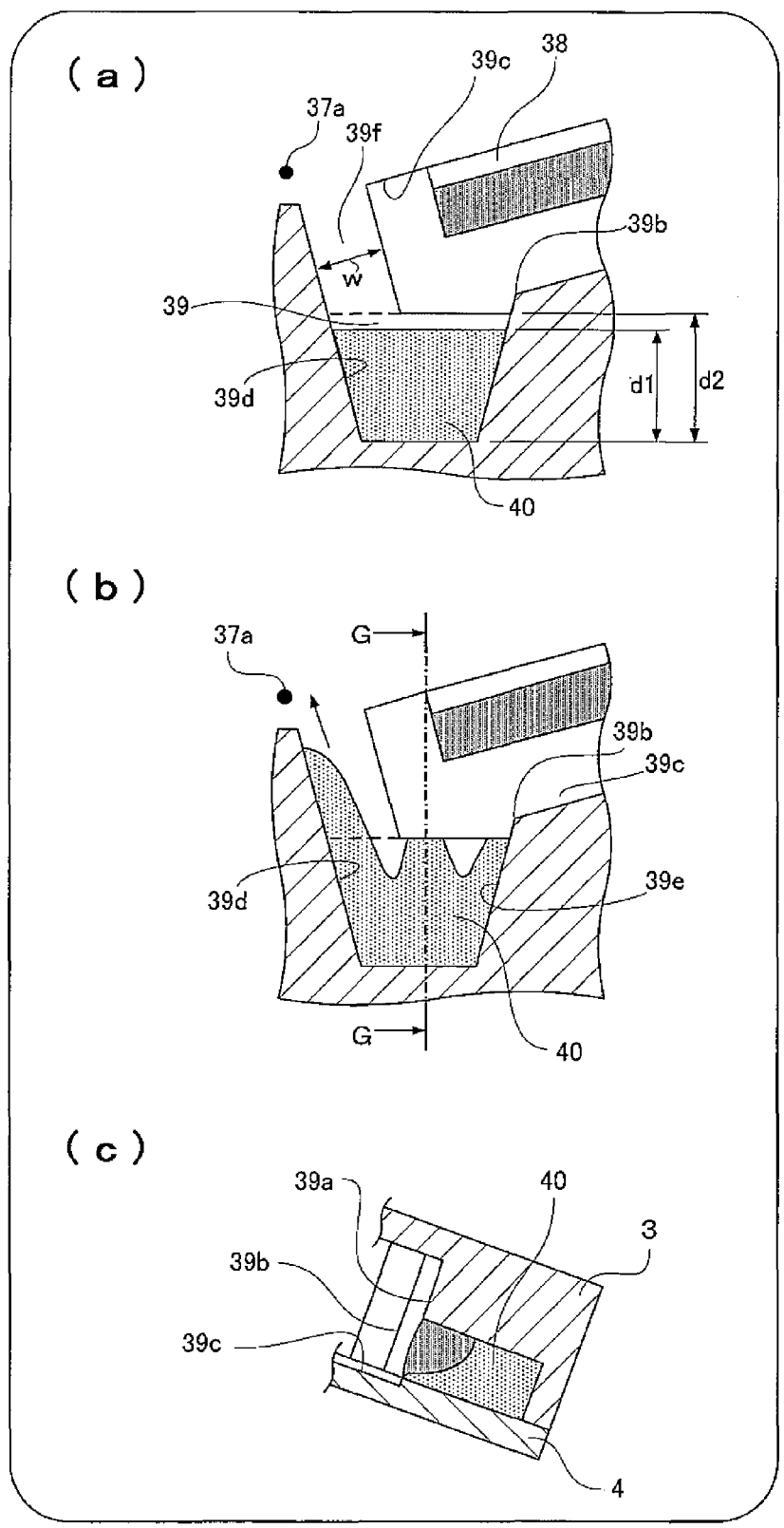
FIG. 30 shows a plan view of a liquid level state of a mixing cavity before the oscillation of an analytical device according to a fourth example of the embodiment, a plan view of a liquid level state of the mixing cavity after oscillation, and a G-G sectional view of the mixing cavity.

For this reason, in the present embodiment, the liquid level is further controlled by the configuration of FIG. 30.

FIG. 30(a) is different from FIG. 29(a) in that the cover substrate 4 includes a recessed section (follow) 39c. The recessed section 39c is formed inside the liquid level (d1) of the diluted plasma 40 and is formed over a region (around the outlet of the measuring passage 38 and a bending section 39b) where the diluted plasma 40 should not spread on the surface of the cover substrate 4. At this point, on a wall surface where an inlet 37a of a capillary tube channel is provided, a region 39f is left that has a width w and includes no recessed sections.

With this configuration, even when the mixing cavity 39 is oscillated, an increase in liquid level to the path having been moistened by the transferred plasma component 18a can be suppressed by a surface tension applied to the level difference of the recessed section 39c, so that the liquid level of the diluted plasma 40 can reach the inlet 37a of the capillary tube channel.

It is more effective to perform water-repellent finish with a repellent or the like on the inner surface of the recessed section 39c formed on the cover substrate 4.

Figure 31:
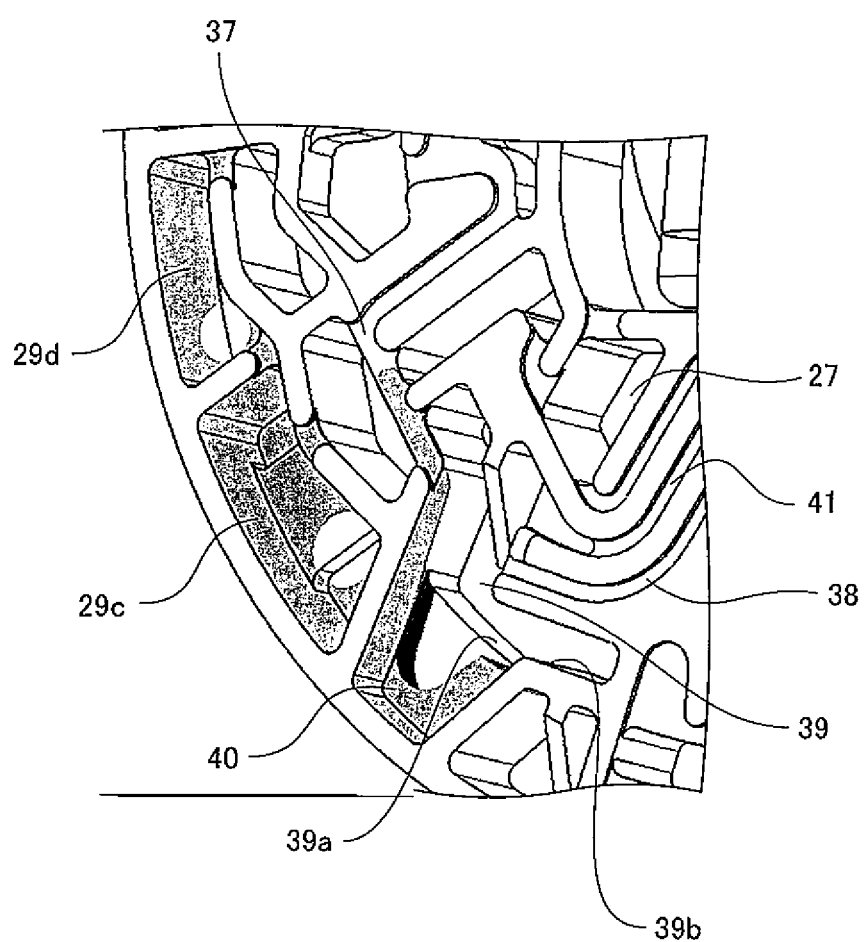
FIG. 31 is an enlarged perspective view showing a liquid level state of the mixing cavity at the start of the suction of diluted plasma from the mixing cavity to a capillary tube channel according to the fourth example.

FIG. 31 shows a state of the liquid level in the mixing cavity 39 at the start of the suction of the diluted plasma 40 from the mixing cavity 39 into a capillary tube channel 37.

Fifth Example

Figure 37:
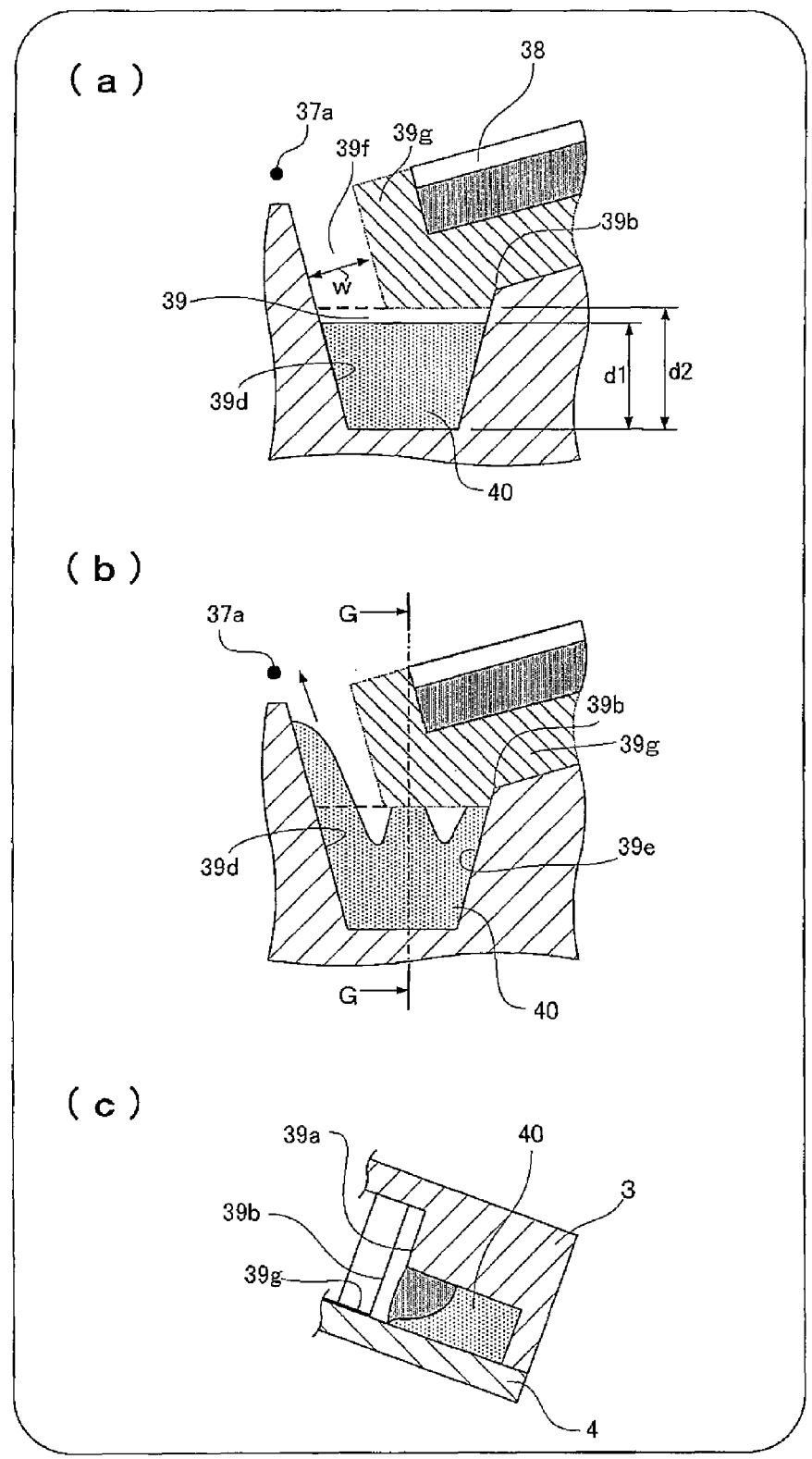
FIG. 37 shows a plan view of a liquid level state of a mixing cavity before the oscillation of an analytical device according to a fifth example, a plan view of a liquid level state of the mixing cavity after oscillation, and a G-G sectional view of the mixing cavity.
Figure 38:
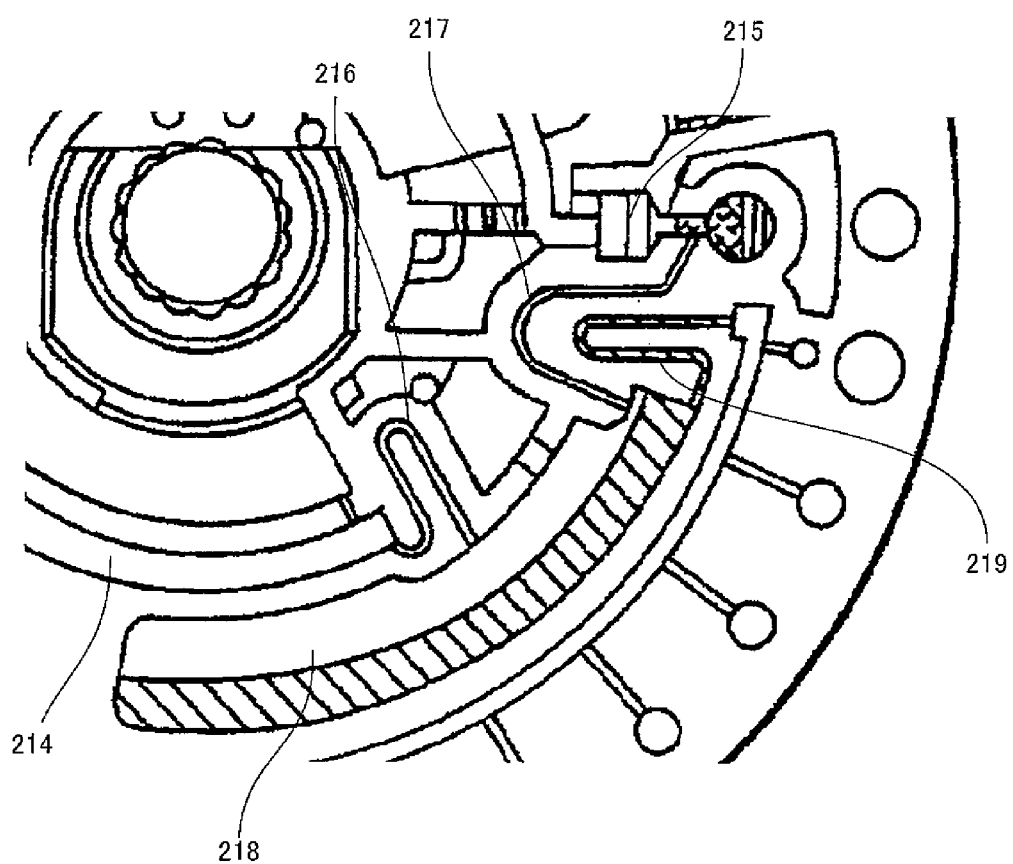
FIG. 38 is a structural diagram of patent literature 1.

In the fourth example, the recessed section 39c is formed on the cover substrate 4 to suppress backflow, whereas in a fifth example of FIG. 37, the recessed section 39c is not formed and a hydrophobic area 39g is formed instead by water-repellent finishing in the area of the recessed section 39c in FIG. 30 illustrating the fourth example, thereby similarly suppressing backflow. In FIG. 37, the hydrophobic area 39g is hatched.

The hydrophobic area 39g effectively suppresses backflow when a bending section 39b is not formed as shown in FIG. 26 and when a level difference 39a is not formed as shown in FIG. 27.

Diluted plasma 40 is efficiently sucked from a mixing cavity 39 by oscillation around the position of FIG. 19(a), and a transport speed in a capillary tube channel 37 is increased by a capillary force and a force of gravity applied to the diluted plasma flowing into the capillary tube channel 37.

In a time period during which the diluted plasma 40 passes through the capillary tube channel 37 and reaches measuring passages 47a, 47b, and 47c, and an overflow passage 47d, repeated oscillations can suppress a surface tension of the diluted plasma 40 in the mixing cavity 39 with an inertial force of oscillations, thereby further increasing the transport speed.

Figure 23:
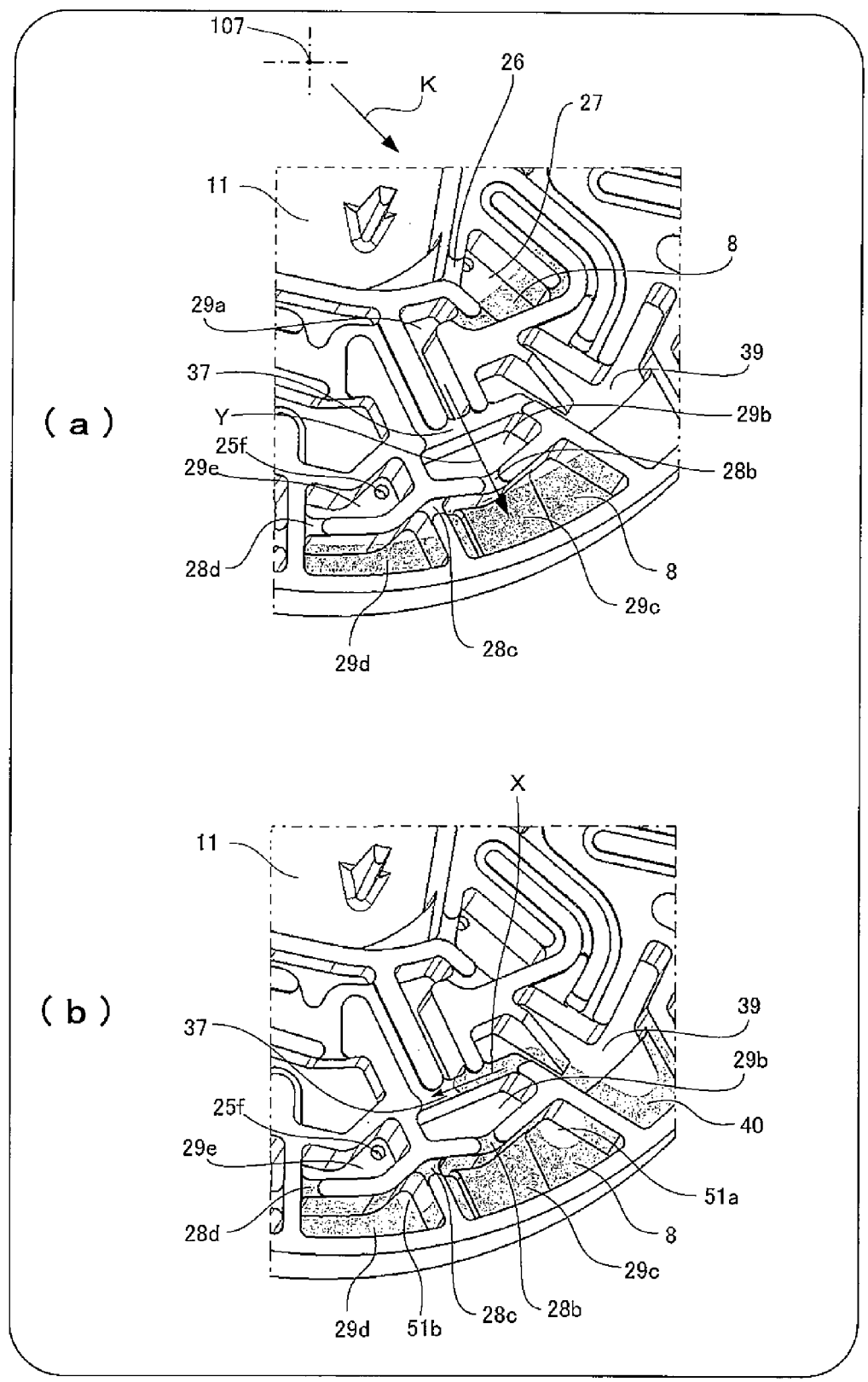
FIG. 23 shows an enlarged perspective view in which the diluent from the diluent container flows into the reserving cavity through a discharging passage in step 2 of the embodiment, and an enlarged perspective view in which the diluted plasma is transferred from the mixing cavity to the subsequent process through a capillary tube channel.
Figure 33:
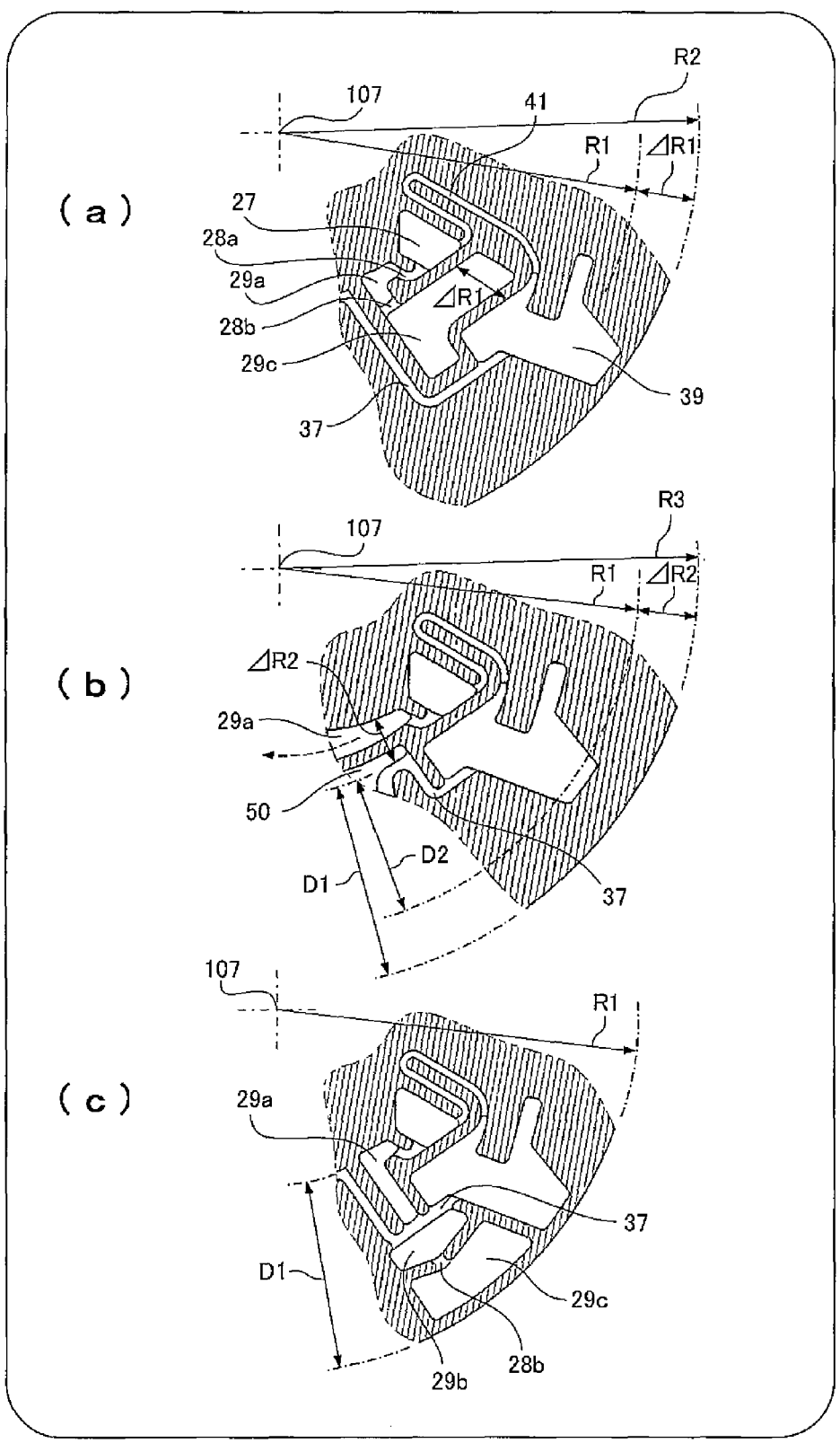
FIG. 33 shows an explanatory drawing of a layout in which the overflow cavity is disposed between the reserving cavity and the mixing cavity according to the embodiment.

Following the explanation of the configuration of the mixing cavity 39 and the transfer method of the solution in accordance with FIGS. 25 to 31, the size reduction of an analytical device 1 of the present embodiment will be described below in accordance with FIGS. 23 and 33.

FIG. 33(a) shows a layout of an overflow cavity 29c disposed between a reserving cavity 27 and the mixing cavity 39.

When a diluent 8 transferred to the reserving cavity 27 exceeds a predetermined quantity, the diluent 8 flows into an overflow cavity 29a through an overflow passage 28a and then flows into the overflow cavity 29c through an overflow passage 28b.

In this configuration, it is necessary to form the overflow cavity 29c next to the outer periphery position of the reserving cavity 27 to reduce the size of the analytical device 1.

In FIG. 33(a), a plasma component 18a and the diluent 8 are transferred from the right of the mixing cavity 39. Thus it is difficult to transfer the mixed diluted plasma 40 from the right of the mixing cavity 39 to the subsequent process and it is necessary to transfer the diluted plasma 40 to the left of the mixing cavity 39.

However, the capillary tube channel 37 has to be extended to the left through the outer periphery of the overflow cavity 29c. Thus the position of the mixing cavity 39 is determined by the radial position of the capillary tube channel 37. Hence, the overflow cavity 29c disposed between the reserving cavity 27 and the mixing cavity 39 expands the outside shape of the analytical device 1 to R2 by a distance ΔR1.

Further, the capillary tube channel 37 disposed on the outer periphery has a long path extended to the inner periphery of the analytical device 1, increasing a loss of the diluted plasma 40.

FIG. 33(b) is a layout showing the overflow cavity 29a extended in a circumferential direction.

Since the overflow cavity 29a is extended in the circumferential direction, the mixing cavity 39 can be disposed next to the reserving cavity 27 on the inner periphery. However, the overflow cavity 29a is shifted to the left and thus an inner position where the capillary tube channel 37 can be extended is shifted to the outer periphery by ΔR2. Thus a space D1 capable of containing the passage and the cavity for the subsequent process is reduced to a space D2 by ΔR2, so that it is difficult to arrange the passage and the cavity. Consequently, the outside shape of the analytical device 1 is increased to R3 by ΔR2.

Therefore, in the present embodiment, the size of the analytical device 1 is reduced by the configuration of FIG. 33(c).

In FIG. 33(c), when the diluent 8 transferred to the reserving cavity 27 exceeds a predetermined quantity, the diluent 8 flows into the overflow cavity 29a through the overflow passage 28a, and then flows toward the outside of the overflow cavity 29a in the radial direction into the overflow cavity 29c, which is disposed at the outermost position, through the capillary tube channel 37, an overflow cavity 29b, and the overflow passage 28b.

The mixing cavity 39 is adjacent to the outer periphery position of the reserving cavity 27, and the capillary tube channel 37 crosses between the overflow cavity 29a and the overflow cavity 29b in the circumferential direction. In other words, in addition to the path for transferring the diluent 8 to the outer periphery by a centrifugal force, another path is provided to transfer the diluent 8 in the circumferential direction by a capillary force.

In this layout, as shown in FIG. 23(a), a centrifugal force is applied along arrow Y in the measurement of the diluent 8. Thus the diluent 8 passing through the overflow cavity 29a is transferred to the overflow cavity 29c without flowing into the mixing cavity 39 connected to one circumferential end of the capillary tube channel 37.

In the case where the diluted plasma 40 is transferred from the mixing cavity 39 to the subsequent process through the capillary tube channel 37, as shown in FIG. 23(b), a capillary force is applied along arrow X. Thus the diluted plasma 40 can be transferred without flowing into the overflow cavities 29a and 29b formed next to the capillary tube channel 37.

At this point, the diluent 8 transferred to the overflow cavity 29c and an overflow cavity 29d is supplied to an overflow passage 28d, the overflow passage 28b, and an overflow passage 28c at the stop of the rotation of the analytical device 1, so that the outlets of the overflow cavities 29c and 29d are sealed from the atmosphere and a negative pressure is generated in the cavities. The overflow passage 28d serves as an atmospheric-side overflow passage connected to an overflow cavity 29e serving as an atmospheric-side overflow cavity communicating with the atmosphere. With this configuration, even when a liquid is transferred from the mixing cavity 39 to the capillary tube channel 37 during oscillation, the diluent 8 does not flow out of the overflow cavity 29c and the diluted plasma 40 can be developed to the subsequent process. In the overflow cavities 29c and 29d, air bubbles 51a and 51b are formed.

Since the analytical device 1 is configured thus according to the present embodiment, a necessary passage pattern can be arranged without using unnecessary regions such as ΔR1 and ΔR2, thereby reducing the size of the analytical device 1.

Further, in the present embodiment, the path for transferring a discharged liquid during the measurement of the diluent 8 crosses the path for transferring the mixed diluted plasma 40 to the subsequent process. The paths are not particularly used for limited processes.

—Step 7—

Further, when the turntable 101 is rotationally driven in the clockwise direction (direction C2), as shown in FIG. 19(b), the diluted plasma 40 retained in the measuring passages 47a, 47b, and 47c overflows at the positions of bending sections 48a, 48b, 48c, and 48d that are connected to an opened-to-atmosphere cavity 50 communicating with the atmosphere, and then only a fixed quantity of the diluted plasma 40 flows into measuring chambers 52b and 52c and a reserving cavity 53.

The diluted plasma 40 retained in the overflow passage 47d at this point flows into an overflow cavity 54 through a backflow preventing passage 55. At this point, the diluted plasma 40 in the capillary tube channel 37 flows into the overflow cavity 29c through the overflow cavity 29b and the overflow passage 28b.

On a part of the side wall of the measuring passage 47a, a recessed section 49 is formed near the bending section 48a so as to communicate with the opened-to-atmosphere cavity 50. Thus the adhesion of a liquid on the wall surface decreases near the bending section 48a, so that the liquid is drained well at the bending section 48a.

A measuring chamber 52a and the measuring chambers 52b and 52c are extended in a direction along which a centrifugal force is applied. To be specific, the measuring chambers are extended from the center of rotation to the outermost periphery of the analytical device 1 so as to have small widths in the circumferential direction of the analytical device 1.

The bottoms of the outer peripheries of the multiple measuring chambers 52a to 52c are arranged at the same radius of the analytical device 1. Thus in the measurement of the measuring chambers 52a to 52c, it is not necessary to provide multiple light sources 112 of the same wavelength and multiple photodetectors 113 at different radius distances for the respective light sources 112, thereby reducing the cost of an apparatus. Since measurement can be conducted using different wavelengths in the same measurement cell, the sensitivity of measurement can be improved by selecting the optimum wavelength according to the concentration of a mixed solution.

Figure 34:
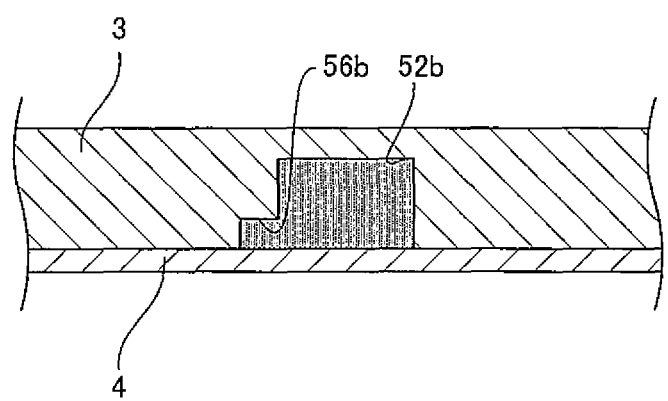
FIG. 34 is a sectional view of the analytical device taken along line F-F of FIG. 19 according to the embodiment.

On one side walls of the measuring chambers 52a to 52c in the circumferential direction, capillary areas 56a to 56c are formed so as to extend from the outer periphery positions to the inner peripheries of the measuring chambers. FIG. 34 is an F-F sectional view of FIG. 19(b).

The suction capacity of the capillary area 56b is not so large as to fully accommodate a sample liquid retained in the measuring chamber 52b. Similarly, the capacities of the capillary areas 56a and 56c are not so large as to fully accommodate a sample liquid retained in the measuring chambers 52a and 52c.

The optical path lengths of the measuring chambers 52a to 52c are adjusted according to the range of absorbance obtained from a mixed solution after a reaction of a component to be tested and reagents.

Figure 35:
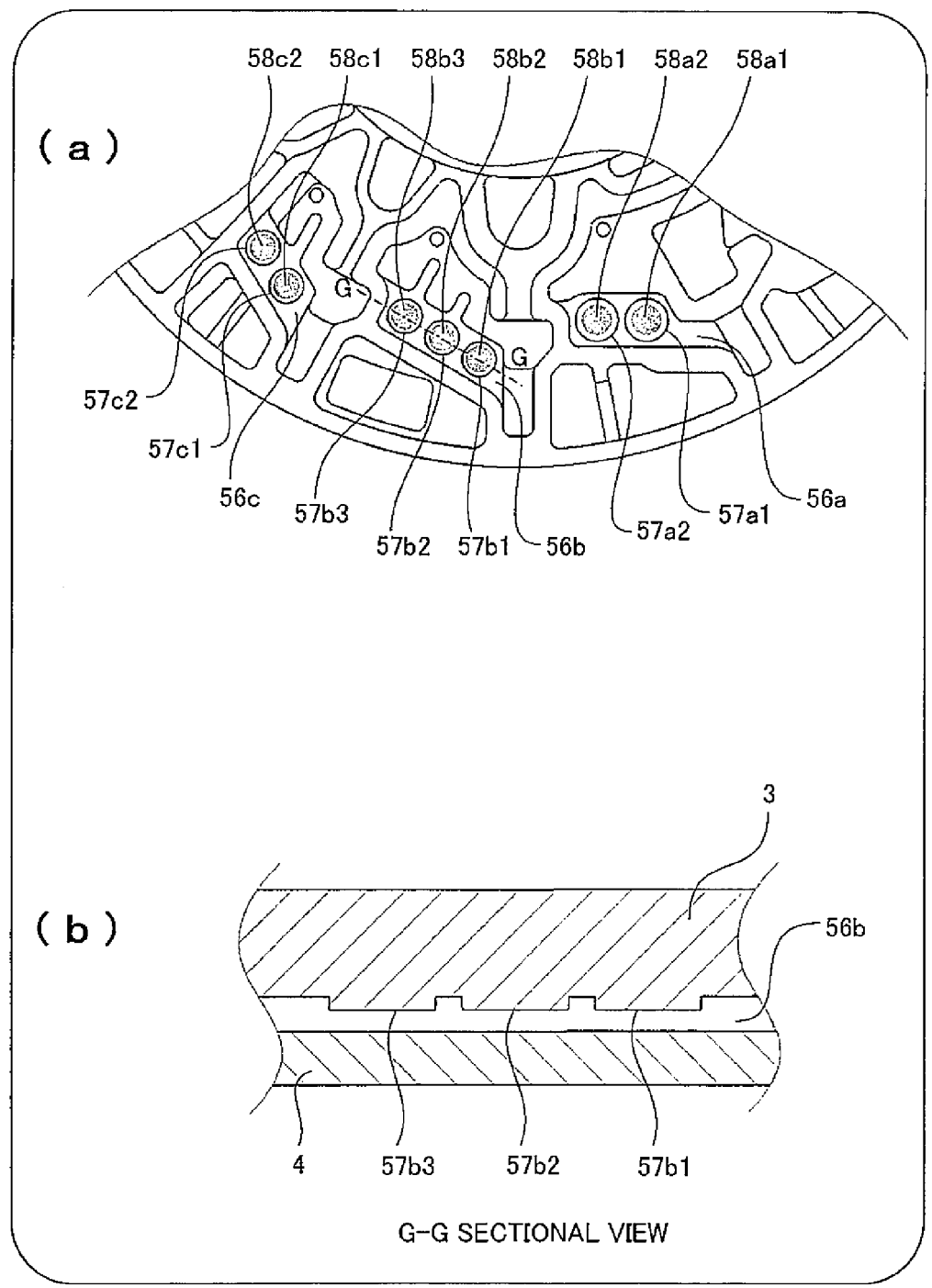
FIG. 35 shows an enlarged plan view of a state of reagents contained in the capillary areas of the analytical device and a G-G sectional view according to the embodiment.

As shown in FIG. 35(a), in the capillary areas 56a, 56b, and 56c, reagents 58a1, 58a2, 58b1, 58b2, 58b3, 58c1, and 58c2 to be reacted with a component to be tested are respectively contained in reagent containing sections 57a1, 57a2, 57b1, 57b2, 57b3, 57c1, and 57c2 formed in the capillary areas 56a, 56b, and 56c. FIG. 35(b) is a G-G sectional view of FIG. 35(a).

The reagent containing sections 57b1, 57b2, and 57b3 are protruded from the capillary area 56b such that a clearance between the reagent containing sections 57b1, 57b2, and 57b3 and the cover substrate 4 is smaller than a clearance between the capillary area 56b and the cover substrate 4.

By applying the reagents 58b1, 58b2, and 58b3 to the reagent containing sections 57b1, 57b2, and 57b3, the expansion of the reagents 58b1, 58b2, and 58b3 can be suppressed by level differences formed by the reagent containing sections 57b1, 57b2, and 57b3 and the capillary area 56b. Thus the different reagents can be contained without being mixed.

The clearance of the reagent containing sections 57b1, 57b2, and 57b3 is smaller than that of the capillary area 56b and thus a liquid sucked into the capillary area 56b is reliably supplied into the reagent containing sections 57b1, 57b2, and 57b3. Consequently, the reagents 58b1, 58b2, 58b3 can be reliably dissolved.

The capillary area 56b has a clearance of about 50 μm to 300 μm, which enables the application of a capillary force. Thus the reagent containing sections 57b1, 57b2, and 57b3 are protruded from the capillary area 56b only by about several tens μm. The capillary areas 56a and 56c have similar configurations.

—Step 8—

Next, the rotation of the turntable 101 is stopped, the analytical device 1 is set at the position of FIG. 20(a), and the turntable 101 is controlled at a frequency of 60 Hz to 120 Hz so as to oscillate the analytical device 1 by about ±1 mm, so that the diluted plasma 40 retained in the reserving cavity 53 is transferred to an operation cavity 61 by the action of a capillary force through a connecting section 59. The connecting section 59 is formed on the side wall of the reserving cavity 53 so as to be immersed under the liquid level of the diluted plasma 40.

Figure 36:
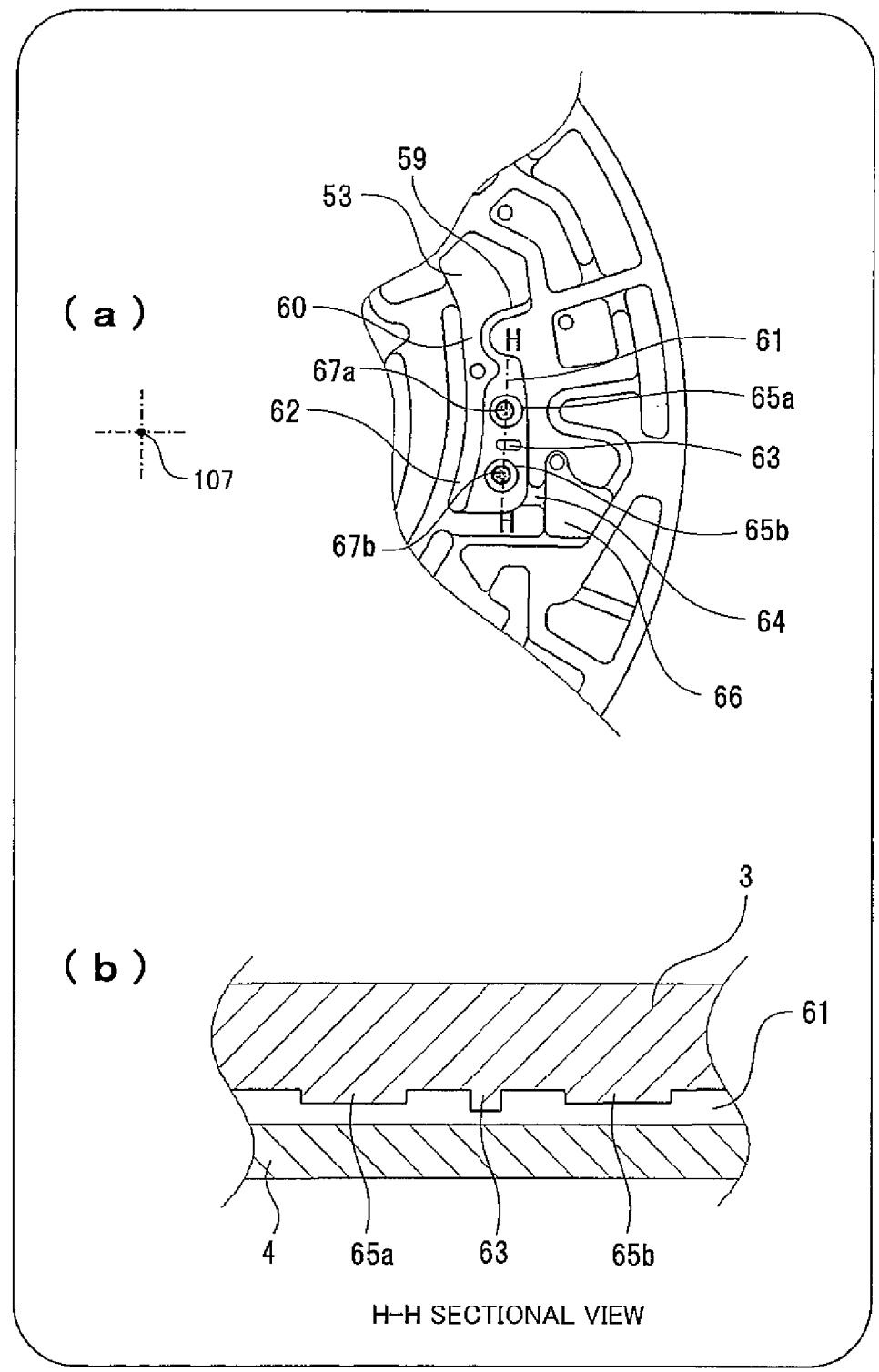
FIG. 36 is an enlarged plan view of a state of reagents contained in the operation cavity of the analytical device and an H-H sectional view according to the embodiment.

Further, the turntable 101 is controlled at a frequency of 120 Hz to 200 Hz to agitate reagents 67a and 67b contained in the operation cavity 61 shown in FIG. 36(a) and the diluted plasma 40, so that a specific component in the diluted plasma 40 is reacted with the reagents.

The diluted plasma 40 transferred to the measuring chambers 52b and 52c is sucked into the capillary areas 56b and 56c by a capillary force as shown in FIG. 20(a). At this point, the reagents 58b1, 58b2, 58b3, 58c1, and 58c2 start dissolving and the specific component in the diluted plasma 40 starts reacting with the reagents.

As shown in FIG. 36(a), the operation cavity 61 is formed next to the reserving cavity 53 in the circumferential direction with respect to the rotation axis 107. A clearance of the operation cavity 61 from the cover substrate 4 enables the application of a capillary force, and the reagents 67a and 67b are contained in reagent containing sections 65a and 65b. In the operation cavity 61, an agitating rib 63 extended in the radial direction is formed around the reagents 67a and 67b, to be specific, between the reagents 67a and 67b.

As shown in FIG. 36(b), the cross sectional dimensions of the agitating rib 63 in the thickness direction of the cover substrate 4 are smaller than the cross sectional dimensions of the operation cavity 61 in the thickness direction of the cover substrate 4.

The reagent containing sections 65a and 65b are protruded from the operation cavity 61 such that a clearance between the reagent containing sections 65a and 65b and the cover substrate 4 is smaller than that of the operation cavity 61 from the cover substrate 4.

Since the clearance of the reagent containing sections 65a and 65b is smaller than that of the operation cavity 61, a liquid flowing into the operation cavity 61 is reliably supplied to the reagent containing sections 65a and 65b. Thus the reagents 67a and 67b can be reliably dissolved. The reagent containing sections 65a and 65b are protruded from the operation cavity 61 by about several tens μm.

On the inner periphery side of the operation cavity 61, a cavity 62 is formed that is connected to the reserving cavity 53 via a communicating section 60. A clearance of the cavity 62 from the cover substrate 4 does not enable the application of a capillary force. Further, the cavity 62 communicates with the atmosphere through an air hole 25h formed near the communicating section 60.

The reserving cavity 53 and the operation cavity 61 are connected via the connecting section 59 that is extended from the side wall of the reserving cavity 53 through the communicating section 60. A clearance of the connecting section 59 from the cover substrate 2 enables the application of a capillary force. In this configuration, the end of the connecting section 59 is circumferentially extended more than the liquid level of the diluted plasma 40 contained in the reserving cavity 53, with respect to the rotation axis.

On the outer periphery of the operation cavity 61, a separating cavity 66 is formed. The separating cavity 66 is connected to the operation cavity 61 via a connecting passage 64. The cross sectional dimensions of the connecting passage 64 from the cover substrate 4 in the thickness direction form a clearance enabling the application of a capillary force. The cross sectional dimensions are regulated so as to have a larger capillary force than that of the operation cavity 61.

Although the space of the operation cavity 61 filled with the diluted plasma 40 is as large as the clearance, a small space 61a not filled with the diluted plasma 40 is left.

In the state of FIG. 20(a), the diluted plasma 40 comes into contact with the reagents 67a and 67b and the reagents 67a and 67b dissolve in the diluted plasma 40. In this state, the analytical device 1 is oscillated by a predetermined angle with respect to the rotation axis 107, so that the diluted plasma 40 in the operation cavity 61 is moved by the space 61a in the operation cavity 61 and collides with the agitating rib 63 during agitation, achieving more reliable agitation. Thus even when the reagents have high specific gravities, it is possible to effectively prevent precipitation of the reagents.

—Step 9—

Next, the turntable 101 is rotationally driven in the clockwise direction (direction C2), so that as shown in FIG. 20(b), the diluted plasma having reacted with the reagents of the operation cavity 61 passes through the connecting passage 64 and flows into the separating cavity 66. Further, the high-speed rotation is kept, so that aggregates generated in the operation cavity 61 are centrifugally separated. In the present embodiment, in a reaction of a component to be inspected and the reagents, a component inhibiting the reaction is removed in an upstream process. By a reaction of the diluted plasma with the reagents in the operation cavity 61, a specific component inhibiting a reaction in a downstream process is coagulated, and the aggregates are removed by centrifugal separation in the subsequent process.

Further, a mixed solution of the reagents retained in the capillary areas 56b and 56c and the diluted plasma is transferred to the outer peripheries of the measuring chambers 52*b* and 52*c* by a centrifugal force, so that the reagents and the diluted plasma are agitated.

In this configuration, the analytical device 1 is repeatedly rotated and stopped to accelerate the agitation of the reagents and the diluted plasma. Thus it is possible to reliably perform agitation in a short time as compared with agitation performed only by diffusion.

—Step 10—

Next, when the rotation of the turntable 101 is stopped, the diluted plasma 40 is sucked into a capillary cavity 69 formed on the wall surface of the separating cavity 66 and flows, as shown in FIG. 21(*a*), into a measuring passage 80 through a connecting passage 70 communicating with the capillary cavity 69, so that a fixed quantity of the diluted plasma 40 is retained.

Moreover, the diluted plasma 40 containing the aggregates in the separating cavity 66 is sucked into a siphon-shaped connecting passage 68 that connects the separating cavity 66 and an overflow cavity 81*a*.

The mixed solution of the reagents and the diluted plasma in the measuring chambers 52*b* and 52*c* is sucked into the capillary areas 56*b* and 56*c* again by a capillary force.

As shown in FIG. 21(*a*), the outermost position of the capillary cavity 69 is extended to the outer periphery of the analytical device 1 so as to be immersed in the diluted plasma retained in the separating cavity 66.

The capillary cavity 69 formed thus preferentially sucks the supernatant diluted plasma rather than a precipitate having a high specific gravity, so that the diluted plasma 40 free of precipitates can be transferred to the measuring passage 80 through the connecting passage 70.

—Step 11—

The turntable 101 is rotationally driven in the clockwise direction (direction C2), so that as shown in FIG. 21(*b*), the diluted plasma 40 retained in the measuring passage 80 overflows at the position of a bending section 84 that is connected to an atmosphere open cavity 83 communicating with the atmosphere, and then only a fixed quantity of the diluted plasma 40 flows into the measuring chamber 52*a*.

Moreover, the diluted plasma 40 in the separating cavity 66, the connecting passage 70, and the capillary cavity 69 flows into the overflow cavity 81*a* through the siphon-shaped connecting passage 68.

The mixed solution of the reagents retained in the capillary areas 56*b* and 56*c* and the diluted plasma is transferred to the outer peripheries of the measuring chambers 52*b* and 52*c* by a centrifugal force, so that the reagents and the diluted plasma are agitated.

In this case, the diluted plasma 40 transferred to the overflow cavity 81*a* is supplied to an overflow passage 82*c* when the rotation of the analytical device 1 is stopped, the overflow passage 82*c* being connected to an overflow cavity 81*b* communicating with the atmosphere. Thus the outlet of the overflow cavity 81*a* is sealed from the atmosphere and a negative pressure is generated in the overflow cavity 81*a*. It is therefore possible to prevent the diluted plasma 40 from flowing from the overflow cavity 81*a* through the connecting passage 68.

—Step 12—

Next, the rotation of the turntable 101 is stopped, so that as shown in FIG. 22(*a*), the diluted plasma 40 transferred to the measuring chamber 52*a* is sucked into the capillary area 56*a* by a capillary force. At this point, the reagents 58*a*1 and 58*a*2 start dissolving and the specific component in the diluted plasma 40 starts reacting with the reagents.

Further, a mixed solution of the reagents and the diluted plasma in the measuring chambers 52*b* and 52*c* is sucked into the capillary areas 56*b* and 56*c* again by a capillary force.

—Step 13—

The turntable 101 is rotationally driven in the clockwise direction (direction C2), so that as shown in FIG. 22(*b*), a mixed solution of the reagents retained in the capillary areas 56*a*, 56*b*, and 56*c* and the diluted plasma is transferred to the outer peripheries of the measuring chambers 52*a*, 52*b*, and 52*c* by a centrifugal force, agitating the reagents and the diluted plasma.

The operations of steps 11 and 12 are repeatedly performed also on the diluted plasma 40 transferred to the measuring chamber 52*a*, accelerating the agitation of the reagents and the diluted plasma 40. Thus it is possible to reliably perform agitation in a short time as compared with agitation performed only by diffusion.

—Step 14—

The analytical device 1 is rotationally driven in a counterclockwise direction (direction C1) or the clockwise direction (direction C2) and the measuring chambers 52*a*, 52*b*, and 52*c* pass between the light source 112 and the photodetector 113. At this point, the arithmetic unit 110 reads a detected value of the photodetector 113 and calculates the concentration of the specific component. When the diluted plasma 40 flows into the measuring chambers 52*a*, 52*b*, and 52*c* in steps 7 and 11, the arithmetic unit 110 reads a detected value of the photodetector 113 during the passage of the measuring chambers 52*a*, 52*b*, and 52*c* between the light source 112 and the photodetector 113, so that absorbance can be calculated before a reaction with the reagents. In the calculation of the arithmetic unit 110, the absorbance is used as the reference data of the measuring chambers 52*a*, 52*b*, and 52*c*, improving the accuracy of measurement.

In the present embodiment, optical access is made in the measuring chamber and a component is measured according to attenuation. A component may be measured by electrically accessing the reactant of a reagent and a sample in the measuring chamber.

In the foregoing embodiments, for the mixing cavity for mixing the sample component and the diluent, the inlet of the passage for feeding a liquid to the measurement spot is formed near one of the wall surfaces of the upper and lower surfaces of the mixing cavity, the upper and lower surfaces being situated between the side walls of the mixing cavity, the side walls being opposed to each other in the direction of oscillation for mixing. Further, the level difference is formed on the other wall surface of the upper and lower surfaces of the mixing cavity such that an inner gap is larger than an outer gap. Moreover, on the other wall surface of the side walls of the mixing cavity, the bending section is formed in a direction along which a distance from the one wall surface increases toward the inner periphery. Furthermore, on the one wall surface of the upper and lower surfaces of the mixing cavity, a groove is formed between the inlet of the passage and the outlet of the passage so as to increase the gap of the mixing cavity, except for a part continuing to the inlet of the passage. The present invention is not limited to a mixing cavity for mixing a sample component and a diluent. The present invention can be similarly implemented for another mixing cavity formed at a location where multiple liquids are received and mixed and then are transferred to measurement spots.

In FIG. 30, the level difference 39*a* is formed on the base substrate 3 and the bending section 39*b* is formed on the side wall 39*e*. In this case, the recessed section 39*c* is formed on the cover substrate 4. Like the recessed section 39*c* formed on the cover substrate 4, backflow is effectively prevented also when the level difference 39a is formed on the base substrate 3 but the bending section 39b is not formed on the side wall 39e as shown in FIG. 26 and when the level difference 39a is not formed on the base substrate 3 but the bending section 39b is formed on the side wall 39e as shown in FIG. 27. Further, backflow can be similarly prevented by forming the hydrophobic area 39g instead of the recessed section 39c on the cover substrate 4.

INDUSTRIAL APPLICABILITY

The present invention is useful for size reduction and the improved performance of an analytical device used for analyzing a component of a liquid collected from an organism or the like.

The invention claimed is:

1. An analytical device rotatable about a rotation axis, comprising:
   a mixing cavity;
   a measurement cell; and
   a first passage that transfers a mixed liquid from the mixing cavity to the measurement cell,
   wherein the mixing cavity, the measurement cell and the first passage have a microchannel structure, the analytical device being configured to perform measurements on the mixed liquid in the measurement cell,
   the mixing cavity comprising:
   an inner surface including a first side wall and a second side wall generally opposite to each other, the first and second side walls being inclined toward each other with increasing distance from the rotation axis; the inner surface of the mixing cavity further including a third wall and a fourth wall generally opposite to each other and extending in the axial direction between the first and second side walls, wherein the mixing cavity is configured to mix a first liquid and a second liquid by a centrifugal force generated by a rotation of the analytical device; and
   a concave step formed on the third wall of the inner surface of the mixing cavity at a location closer to the rotation axis such that a first thickness of the mixing cavity at a location further away from the rotation axis is smaller than a second thickness of the mixing cavity at the concave step,
   wherein an inlet of the first passage is positioned at a location adjacent a radially inner side of the mixing cavity, the inlet of the first passage being positioned closer to one of the first and second side walls than the other, and closer to one of the third and fourth walls than the other.

2. The analytical device according to claim 1, further comprising:
   a second passage that feeds the first liquid to the mixing cavity, the second passage having an outlet from which the first liquid is fed into the mixing cavity from the second passage; and
   a recessed section formed on one of the third and fourth walls of the mixing cavity, except for a part continuing to the inlet of the first passage, such that the second thickness of the mixing cavity increases at the recessed section.

3. The analytical device according to claim 1, further comprising:
   a second passage that feeds the first liquid to the mixing cavity, the second passage having an outlet from which the first liquid is fed into the mixing cavity from the second passage; and
   a recessed section formed on one of the third and fourth walls of the mixing cavity, except for a part continuing to the inlet of the first passage, such that the second thickness of the mixing cavity increases at the recessed section, the recessed section having a water-repellent inner surface.

4. The analytical device according to claim 1, further comprising:
   a second passage that feeds the first liquid to the mixing cavity, the second passage having an outlet from which the first liquid is fed into the mixing cavity from the second passage; and
   a water repellent area formed on one of the third and fourth walls of the mixing cavity, except for a part continuing to the inlet of the first passage.

5. An analytical device rotatable about a rotation axis, comprising:
   a mixing cavity;
   a measurement cell; and
   a first passage that transfers a mixed liquid from the mixing cavity to the measurement cell,
   wherein the mixing cavity, the measurement cell and the first passage have microchannel structure, the analytical device being configured to perform measurements on the mixed liquid in the measurement cell,
   the mixing cavity comprising:
   an inner surface including a first side wall and a second side wall generally opposite to each other, the first and second side walls being inclined toward each other with increasing distance from the rotation axis; the inner surface of the mixing cavity further including a third wall and a fourth wall generally opposite to each other and extending in the axial direction between the first and second side walls, wherein the mixing cavity is configured to mix a first liquid and a second liquid by a centrifugal force generated by a rotation of the analytical device; and
   a bending section formed on one of the first and second side walls of the mixing cavity, the bending section extending radially outwardly with decreasing distance from the rotation axis such that a distance between the first and second side walls becomes larger toward the rotation axis,
   wherein an inlet of the first passage is positioned at a location adjacent a radially inner side of the mixing cavity, the inlet of the first passage being positioned closer to one of the first and second side walls than the other, and closer to one of the third and fourth walls than the other.

6. The analytical device according to claim 5, further comprising:
   a second passage that feeds the first liquid to the mixing cavity, the second passage having an outlet from which the first liquid is fed into the mixing cavity from the second passage; and
   a recessed section formed on one of the third and fourth walls of the mixing cavity, except for a part continuing to the inlet of the first passage, such that a thickness of the mixing cavity increases at the recessed section.

7. The analytical device according to claim 5, further comprising:
   a second passage that feeds the first liquid to the mixing cavity, the second passage having an outlet from which the first liquid is fed into the mixing cavity from the second passage; and
   a recessed section formed on one of the third and fourth walls of the mixing cavity, except for a part continuing to the inlet of the first passage, such that a thickness of the mixing cavity increases at the recessed section, the recessed section having a water-repellent inner surface.

8. The analytical device according to claim 5, further comprising:
a second passage that feeds the first liquid to the mixing cavity, the second passage having an outlet from which the first liquid is fed into the mixing cavity from the second passage; and
a water repellent area formed on one of the third and fourth walls of the mixing cavity, except for a part continuing to the inlet of the first passage.

9. An analytical device rotatable about a rotation axis, comprising:
a mixing cavity;
a measurement cell; and
a first passage which transfers a mixed liquid from the mixing cavity to the measurement cells,
wherein the mixing cavity, the measurement cell and the first passage have a microchannel structure, the analytical device being configured to perform measurements on the mixed liquid in the measurement cell,
the mixing cavity comprising:
an inner surface including a first side wall and a second side wall generally opposite to each other, the first and second side walls being inclined toward each other with increasing distance from the rotation axis; the inner surface of the mixing cavity further including a third wall and a fourth wall generally opposite to each other and extending in the axial direction between the first and second side walls, wherein the mixing cavity is configured to mix a first liquid and a second liquid by a centrifugal force generated by a rotation of the analytical device;
a concave step formed on the third wall of the inner surface of the mixing cavity at a location closer to the rotation axis such that a first thickness of the mixing cavity at a location further away from the rotation axis is smaller than a second thickness of the mixing cavity at the concave step; and
a bending section formed on one of the first and second side walls of the mixing cavity, the bending section extending radially outwardly with decreasing distance from the rotation axis such that a distance between the first and second side walls becomes larger toward the rotation axis,
wherein an inlet of the first passage is positioned at a location adjacent a radially inner side of the mixing cavity, the inlet of the first passage being positioned closer to one of the first and second side walls than the other, and closer to one of the third and fourth walls than the other.

10. The analytical device according to claim 9, further comprising:
a second passage that feeds the first liquid to the mixing cavity, the second passage having an outlet from which the first liquid is fed into the mixing cavity from the second passage; and
a recessed section formed on one of the third and fourth walls of the mixing cavity, except for a part continuing to the inlet of the first passage, such that the second thickness of the mixing cavity increases at the recessed section.

11. The analytical device according to claim 9, further comprising:
a second passage that feeds the first liquid to the mixing cavity, the second passage having an outlet from which the first liquid is fed into the mixing cavity from the second passage; and
a recessed section formed on one of the third and fourth walls of the mixing cavity, except for a part continuing to the inlet of the first passage, such that the second passage of the mixing cavity increases at the recessed section, the recessed section having a water-repellent inner surface.

12. The analytical device according to claim 9, further comprising:
a second passage that feeds the first liquid to the mixing cavity, the second passage having an outlet from which the first liquid is fed into the mixing cavity from the second passage; and
a water repellent area formed on one of the third and fourth walls of the mixing cavity, except for a part continuing to the inlet of the first passage.

* * * * *